US008082188B2

United States Patent
Shinohara et al.

(10) Patent No.: US 8,082,188 B2
(45) Date of Patent: *Dec. 20, 2011

(54) LENS ORDER SYSTEM, LENS ORDER METHOD, LENS ORDER PROGRAM AND RECORDING MEDIUM STORING THE LENS ORDER PROGRAM

(75) Inventors: Toshihide Shinohara, Chinoshi (JP); Tadashi Kaga, Minowa-machi (JP); Ayumu Ito, Minowa-machi (JP)

(73) Assignee: Seiko Epson Corporation, Tokyo (JP)

( * ) Notice: Subject to any disclaimer, the term of this patent is extended or adjusted under 35 U.S.C. 154(b) by 1174 days.

This patent is subject to a terminal disclaimer.

(21) Appl. No.: 11/882,507

(22) Filed: Aug. 2, 2007

(65) Prior Publication Data

US 2008/0033836 A1 Feb. 7, 2008

(30) Foreign Application Priority Data

Aug. 3, 2006 (JP) ................................ 2006-212231

(51) Int. Cl.
*G06Q 30/00* (2006.01)
(52) U.S. Cl. ............ 705/26.82; 705/27.1; 703/1; 703/6; 703/11; 715/757; 351/200; 351/158; 351/2
(58) Field of Classification Search ............... 705/26.82, 705/27.2; 703/1, 6, 11; 715/757, 1, 6, 11; 351/200, 158, 2
See application file for complete search history.

(56) References Cited

U.S. PATENT DOCUMENTS

| 5,280,570 | A | * | 1/1994 | Jordan | ............................ | 345/632 |
| 6,142,628 | A | * | 11/2000 | Saigo | ............................. | 351/204 |
| 6,329,989 | B1 | * | 12/2001 | Qi et al. | ......................... | 345/428 |

(Continued)

FOREIGN PATENT DOCUMENTS

EP 1 468 649 A1 10/2004

(Continued)

OTHER PUBLICATIONS

BusinessWire, "MIT Student Inventor Sees Clear Future in 'Desktop Printer' for Low- Cost Eyeglass Lenses" dated Feb. 19, 2004.*

(Continued)

*Primary Examiner* — Mark Fadok
(74) *Attorney, Agent, or Firm* — Sughrue Mion, PLLC

(57) ABSTRACT

A lens order system, includes: a server unit including: a data recognizer that recognizes lens design detail data on setting details of a lens; an image data recognizer that recognizes image data on an image; a lens design section that designs the lens based on the lens design detail data; an image processor that creates processed image data in which lens image data on an image of the designed lens is superposed on the image data and a superposing portion of the image data and the lens image data is image-processed to show a vision of the image data through the designed lens; and an order reception section that recognizes order data on an order of the designed lens and generates order reception data; and a terminal unit connected with the server unit in a data transmittable manner, the terminal unit including: a data acquiring section that acquires the lens design detail data; a display controller that recognizes and displays on a display the processed image data sent from the server unit; and an order section that generates the order data.

7 Claims, 15 Drawing Sheets

U.S. PATENT DOCUMENTS

| | | | |
|---|---|---|---|
| 6,813,536 B1 * | 11/2004 | Gottschald | 700/160 |
| 7,167,771 B2 | 1/2007 | Ito | |
| 7,287,853 B2 * | 10/2007 | Toshima et al. | 351/205 |
| 7,914,148 B2 * | 3/2011 | Fisher et al. | 351/233 |
| 2001/0026351 A1 | 10/2001 | Gao et al. | |
| 2004/0017499 A1 * | 1/2004 | Ambiru | 348/333.12 |
| 2005/0073650 A1 * | 4/2005 | Ito | 351/200 |

FOREIGN PATENT DOCUMENTS

| | | |
|---|---|---|
| EP | 1 515 179 A1 | 3/2005 |
| JP | 4-148906 A | 5/1992 |
| JP | 10-115808 A | 5/1998 |
| JP | 11-119172 A | 4/1999 |
| JP | 11-120213 A | 4/1999 |
| JP | 11-142797 A | 5/1999 |
| JP | 11-183856 A | 7/1999 |
| JP | 2000-29377 A | 1/2000 |
| JP | 2000-47153 A | 2/2000 |
| JP | 2000-47154 A | 2/2000 |
| JP | 2000-47155 A | 2/2000 |
| JP | 2001-297323 A | 10/2001 |
| JP | 2005-91425 A | 4/2005 |
| JP | 2005-308490 A | 11/2005 |
| JP | 2006-343778 A | 12/2006 |
| WO | 03/081536 A1 | 10/2003 |

OTHER PUBLICATIONS

Yen et al., "Web-based Virtual Reality Catalog in Electronic Commerce", Proceedings of the 33rd Hawaii International Conference on System Sciences—2000.

* cited by examiner

LENS ORDER SYSTEM, LENS ORDER METHOD, LENS ORDER PROGRAM AND RECORDING MEDIUM STORING THE LENS ORDER PROGRAM

The entire disclosure of Japanese Patent Application No. 2006-212231, filed Aug. 3, 2006, is expressly incorporated by reference herein.

BACKGROUND

1. Technical Field

The present invention relates to a lens order system, a lens order method, a lens order program and a recording medium storing the lens order program by which a lens such as a spectacles lens is ordered.

2. Related Art

A lens design system has been known, in which design data of a lens is input in a terminal unit provided in a shop to be sent to a server unit provided on a manufacturer facility, where the lens is designed based on the lens design data received by the server unit (see, for example, JP-A-H10-115808).

In the system disclosed in JP-A-H10-115808, lens prescription data and a lens usage purpose of a spectacles lens user are input in the terminal unit. A computer of the terminal unit selects an optimal lens in accordance with lens evaluation data based on the input data and displays the lens on a display unit, the selected lens being online-ordered to the manufacturer.

In the above-described architecture, it is not possible to check an actual vision of the lens user with the ordered lens, so that the manufactured lens may not match the client.

To solve this problem, the terminal unit may be provided with simulation software for simulating on a display area of the display unit the lens user's vision with the ordered lens such that the lens user can order the lens after checking an actual vision through the lens.

However, since such simulation software contains a large volume of information, when the software is installed on the terminal unit, operations on the terminal unit will be cumbersome and larger processing load will be placed on the terminal unit. To avoid the problem, a higher-performance terminal unit capable of processing the simulation software may be provided at shops. However, this measure will increase the cost and make procedure at shops cumbersome, resulting in inefficiency.

SUMMARY

An advantage of some aspects of the present invention is to provide, in consideration of the above described problems, a lens order system, a lens order method, a lens order program and a recording medium storing the lens order program by which a lens suitable for a lens user can be easily ordered.

A lens order system according to an aspect of the invention includes: a server unit and a terminal unit connected with the server unit in a data transmittable manner. The server unit includes: a data recognizer that recognizes lens design detail data on setting details of a lens; an image data recognizer that recognizes image data on an image; a lens design section that designs the lens based on the lens design detail data; an image processor that creates processed image data in which lens image data on an image of the designed lens is superposed on the image data and a superposing portion of the image data and the lens image data is image-processed to show a vision of the image data through the designed lens; and an order reception section that recognizes order data on an order of the designed lens and generates order reception data. The terminal unit includes: a data acquiring section that acquires the lens design detail data; a display controller that recognizes and displays on a display the processed image data sent from the server unit; and an order section that generates the order data.

According to the aspect of the invention, the server unit includes the data recognizer that recognizes lens design detail data, the image data recognizer that recognizes recognizing image data, the lens design section that designs a lens, the image processor that generates processed image data in which lens image data is superposed on the image data and an image of a superposing portion is image-processed to show the vision of the image data through the designed lens and the order reception section that recognizes order data and generates order reception data.

The terminal unit includes the data acquiring section acquiring lens design detail data, the display controller recognizing the processed image data and controlling the display to display the processed image data and the order section generating order data.

Accordingly, in the server unit, the lens image data is superposed on the image data and the processed image data in which the superposing portion is image-processed to show the lens user's vision of the image data through the lens, and the processed image data is sent to the terminal unit to be displayed on the display. Hence, the lens user can check the vision through the lens manufactured based on the prescription input as the lens design detail data before the lens is actually manufactured and delivered. Based on the processed image data, the lens design detail data can be corrected and the lens user can check the processed image data re-sent from the server unit, so that it is possible to provide most appropriate design of the lens that is suitable for the lens user and order such an appropriate lens.

To receive the processed image data sent from the server unit on the terminal unit, it is only necessary for the user to input the lens design detail data through an input operation and the like such that the lens design detail data is acquired by the data acquiring section and sent to the server unit, thereby facilitating an operation on the terminal unit. Since the terminal unit only needs to reproduce the processed image data sent from the server unit, the processing load placed on the terminal unit can be reduced, thereby improving the performance of the terminal unit. Data to be sent from the terminal unit to the server unit is only the lens design detail data and the order data while data to be sent from the server unit to the terminal unit is only the processed image data generated by the server unit, so that communication load between the terminal unit and the server unit can be reduced, thereby shortening communication time. Hence, the input operation of the lens design detail data or the checking process of the processed image data can be conducted on the terminal unit in a smooth manner.

In the lens order system according the aspect of the invention, the lens design detail data may include lens prescription data on a prescription for a lens of a lens user, and the lens design section may design the lens based on the lens prescription data.

According to the aspect of the invention, the lens design section designs the lens based on the lens prescription data of the lens design detail data. Hence, the lens design section can design the lens that matches the lens prescription desired by the lens user. Since the image processor creates the processed image data based on the designed lens, the lens user can easily check the vision through the lens matching the lens prescription data by the processed image data reproduced on the terminal unit. Hence, since the lens user can easily check the desired lens before manufacturing the lens, it is possible to manufacture the lens as desired by the lens user.

In the lens order system according to the aspect of the invention, the lens design detail data may include vision data on a vision of the lens user, and the image processor may superpose the lens image data on the image data corresponding to the vision of the lens user based on the vision data and image-processes the superposing portion of the image data and the lens image data to show the vision of the image data of the lens user through the designed lens.

The image processor creates, based on the vision data of the lens design detail data, the processed image data in which the lens image data is superposed on the image data corresponding to the vision of the lens user. Accordingly, by reproducing the processed image data on the terminal unit, the lens user can check both the naked-eye vision of the image data and the vision of the image data through the lens. Thus, it is easy to check the vision with the lens will be by comparing with the vision seen with naked eyes, so that the lens user can easily check the performance of the lens or whether or not the lens matches with his preference and the lens user can order a lens more suitable for the lens user.

Herein, the server unit may includes an image data storage storing plural pieces of the image data corresponding to the vision of the lens user, and the image data recognizer may recognize the image data corresponding to the vision of the lens user based on the vision data.

According to the aspect of the invention, the image data recognizer of the server unit recognizes the image data corresponding to the vision data of the lens user from the image data storage. The image processor can easily generate the processed image data only by superposing the lens image data on the recognized image data and image-processing the superposing portion. Hence, the processing load for the image processing of the image data can be reduced, thereby reducing the processing load placed on the server unit. Since the server unit is provided with the image data storage, the terminal unit may not have an area for storing the image data, thereby preventing a storage such as a hard disc of each terminal unit from being too excessively consumed. Thus, the lens order system can be used even in the terminal unit only having a small storage area.

Alternatively, in the lens order system according to the aspect of the invention, the image processor may be adapted to generate based on the vision data the processed image data in which the image data is image-processed to show the lens user's vision of the image data with naked eyes, superpose the lens image data on the generated processed image data and image-process the superposing portion of the processed image data and the lens image data to show the lens user's vision of the image data through the designed lens.

According to the aspect of the invention, the image processor creates, based on the vision data of the image data, the processed image data in which the lens image data is superposed on the processed image data image-processed to show the lens user's vision of the image data with naked eyes. Accordingly, since the image processor creates the processed image data based on the vision data of the lens user, the volume of the image data stored in the image data storage for storing image data such as a hard disc can be reduced, thereby promoting more efficient use of a disc area of the hard disc of the server unit.

In the lens order system according to the aspect of the invention, the lens design detail data may include lens form design data on a design of a lens form, and the lens design section may design the lens into a form based on the lens form design data.

According to the aspect of the invention, the lens design section designs the lens based on the lens form design data. Hence, the lens can be designed into a form that the lens user desires. Since the image processor superposes the lens image data of the lens designed in accordance with the lens form design data on the image data, the lens user can judge whether or not the lens form is suitable before the lens is manufactured only by checking the processed image data. Accordingly, the lens having an appropriate form that fits the lens user can be ordered.

In the lens order system according to the aspect of the invention, the lens design detail data may include lens usage purpose data on a usage purpose of the lens of the lens user, the lens design section may design the lens corresponding to the usage purpose of the lens based on the lens usage purpose data, and the image data recognizer may recognize the image data corresponding to the usage purpose of the lens based on the lens usage purpose data.

According to the aspect of the invention, the lens design section designs the lens corresponding to the lens usage purpose data, and the image data recognizer recognizes the image data corresponding to the lens usage purpose data. For example, when the lens usage purpose data indicates the use for deskwork, the lens design section designs the lens for near distance lens, and the image data recognizer recognizes the image data in which an image of newspaper or a display screen or a keyboard of a personal computer is disposed in the reach of the lens user. When data indicating that the lens is used for a far distance purpose such as playing golf and bird watching is stored as the lens usage purpose data, the lens design section designs the lens for far vision and the image data recognizer recognizes the image data in which an image such as a mountain and a building is disposed apart from the lens user by a predetermined distance or more.

Accordingly, since the lens design section designs the lens corresponding to the lens usage purpose of the lens user, it is possible to more appropriately design the lens as the lens user desires. Since the image data recognizer recognizes the image data in which the image is disposed at a position corresponding to the lens usage purpose of the lens user, it is possible to generate the processed image data by the image processor with image data disposed in accordance with the lens usage purpose data. By superposing the lens image data on the image data, the lens user can check the processed image data when the image corresponding to the usage purpose is seen through the lens. Hence, the lens user can select a lens suitable for the usage purpose of the lens before manufacturing the lens, so that a more appropriate lens can be ordered.

Herein, in the lens order system according to the aspect of the invention, the lens usage purpose data may be usage distance data on a distance from a to-be-seen object to the lens user wearing the lens.

According to the aspect of the invention, the lens usage purpose data includes the usage distance data on a distance from the lens to the to-be-seen object. Accordingly, since the distance between the lens and the to-be-seen object is clearly recognized, the lens design section can more reliably design the lens in accordance with the lens usage purpose and the image data recognizer can recognize the image data in which an image is disposed at a distance by the distance from the lens to the to-be-seen object. Hence, the lens can be designed more appropriately as the lens user desires, and the processed image data can be more appropriately generated.

In the lens order system according to the aspect of the invention, the image processor may superpose the lens image data on the image data and generates motion picture data moved on the image data.

According to the aspect of the invention, the image processor generates the motion picture data in which the lens image data is moved on the image data. Accordingly, it is possible to simulate distortion and the like generated by the movement of the lens while the lens user sees the image with the lens corresponding to the design lens data. Hence, owing to the motion picture data, it is possible to more appropriately simulate the usage of the lens. Thus, it is possible to more appropriately assist the lens user in ordering the lens, so that a lens more appropriate for the lens user can be ordered.

A lens order method according to an aspect of the invention, includes: in a terminal unit connected with a server unit in a data transmittable manner, acquiring lens design detail data and sending the acquired lens design detail data to the server unit; in the server unit, recognizing lens design detail data on setting details of a lens sent from the terminal unit, recognizing image data on an image; designing the lens based on the lens design detail data, superposing lens image data on an image of the designed lens on the image data; image-processing a superposing portion of the image data and the lens image data to show a vision of the image data through the designed lens; and sending the processed image data to the terminal unit; in the terminal unit, recognizing the processed image data sent from the server unit to be displayed by a display; generating order data on an order of the designed lens; and sending the generated order data to the server unit; and in the server unit, receiving the order data and generating received data.

According to the aspect of the invention as describe above, in the server unit, the lens image data is superposed on the image data and the processed image data is generated by image-processing the superposing portion to show the lens user's vision of the image data through the lens, and the processed image data is sent to the terminal unit to be displayed on the display. Hence, the lens user can check the vision with the ordered lens before the lens is actually manufactured and delivered. Based on the processed image data, the lens design detail data can be corrected and the lens user can check the processed image data re-sent from the server unit, so that the lens user can design the most appropriate lens suitable for the lens user and order the best lens.

In the terminal unit, only by inputting the lens design detail data to be sent to the server unit by an input operation and the like such that the lens design detail data that the data acquiring section acquires by the input operation is sent to the server unit, the processed image data can be sent from the server unit, thereby facilitating an operation on the terminal unit. Since the terminal unit only needs to reproduce the processed image data sent from the server unit, the processing load placed on the terminal unit can be reduced, thereby improving the performance of the terminal unit. Data to be sent from the terminal unit to the server unit is only the lens design detail data and the order data while data to be sent from the server unit to the terminal unit is only the processed image data generated by the server unit, so that communication load between the terminal unit and the server unit can be reduced and communication time can be shortened. Hence, the input operation of the lens design detail data or the checking of the processed image data can be conducted on the terminal unit in a smooth manner.

A lens order program according to an aspect of the invention operates a computer as the above-described lens order system.

According to the aspect of the invention, the lens order program operates a computer as the above-described lens order system. Hence, as described above, the lens user can check the vision with the ordered lens before the lens is actually manufactured and delivered, so that the lens can be designed most appropriately for the lens user and a suitable lens can be ordered. An operation on the terminal unit can be made easy and the processing load placed on the terminal unit can be reduced, thereby improving the performance of the terminal unit. In addition, the communication load between the terminal unit and the server unit can be reduced and the communication time can be shortened.

A lens order program according to an aspect of the invention operates a computer to perform the above-described lens order method.

According to the aspect of the invention, the lens order program operates a computer as the above-described lens order system. Hence, as described above, the lens user can check the vision with the ordered lens before the lens is actually manufactured and delivered, so that the lens can be designed most appropriately for the lens user and a suitable lens can be ordered. An operation on the terminal unit can be made easy and the processing load placed on the terminal unit can be reduced, thereby enabling more smooth operation on the terminal unit. In addition, the communication load between the terminal unit and the server unit can be reduced and the communication time can be shortened.

A recording medium according to an aspect of the invention stores the above-described lens order program in a manner readable by a computer.

According to the aspect of the invention, the recording medium stores the above-described lens order program in a manner readable by a computer. Hence, the computer can execute the lens order program only by operating the computers of the server unit and the terminal unit to read the recording medium.

BRIEF DESCRIPTION OF THE DRAWINGS

The invention will be described with reference to the accompanying drawings, wherein like numbers reference like elements.

DESCRIPTION OF EXEMPLARY EMBODIMENT(S)

Figure 1:
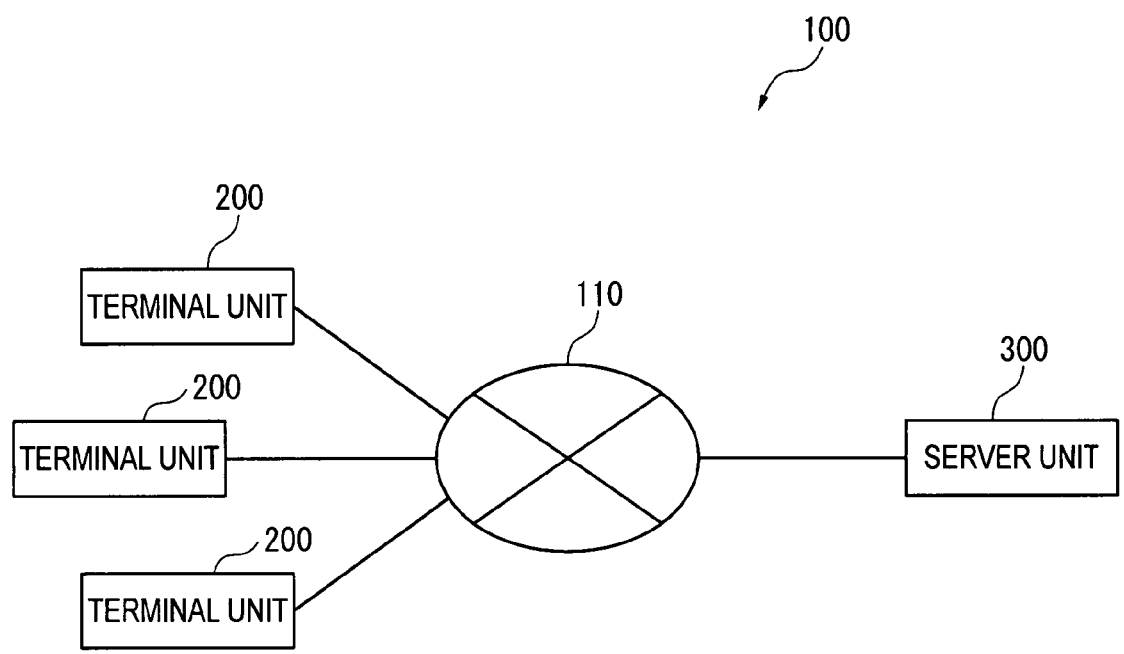
FIG. 1 is a block diagram schematically showing an overall architecture of a lens order system according to an exemplary embodiment of the invention.

A lens order system according to an exemplary embodiment of the invention will be described below with reference to the drawings. FIG. 1 is a block diagram schematically showing an overall architecture of the lens order system according to the exemplary embodiment of the invention.

Figure 2:
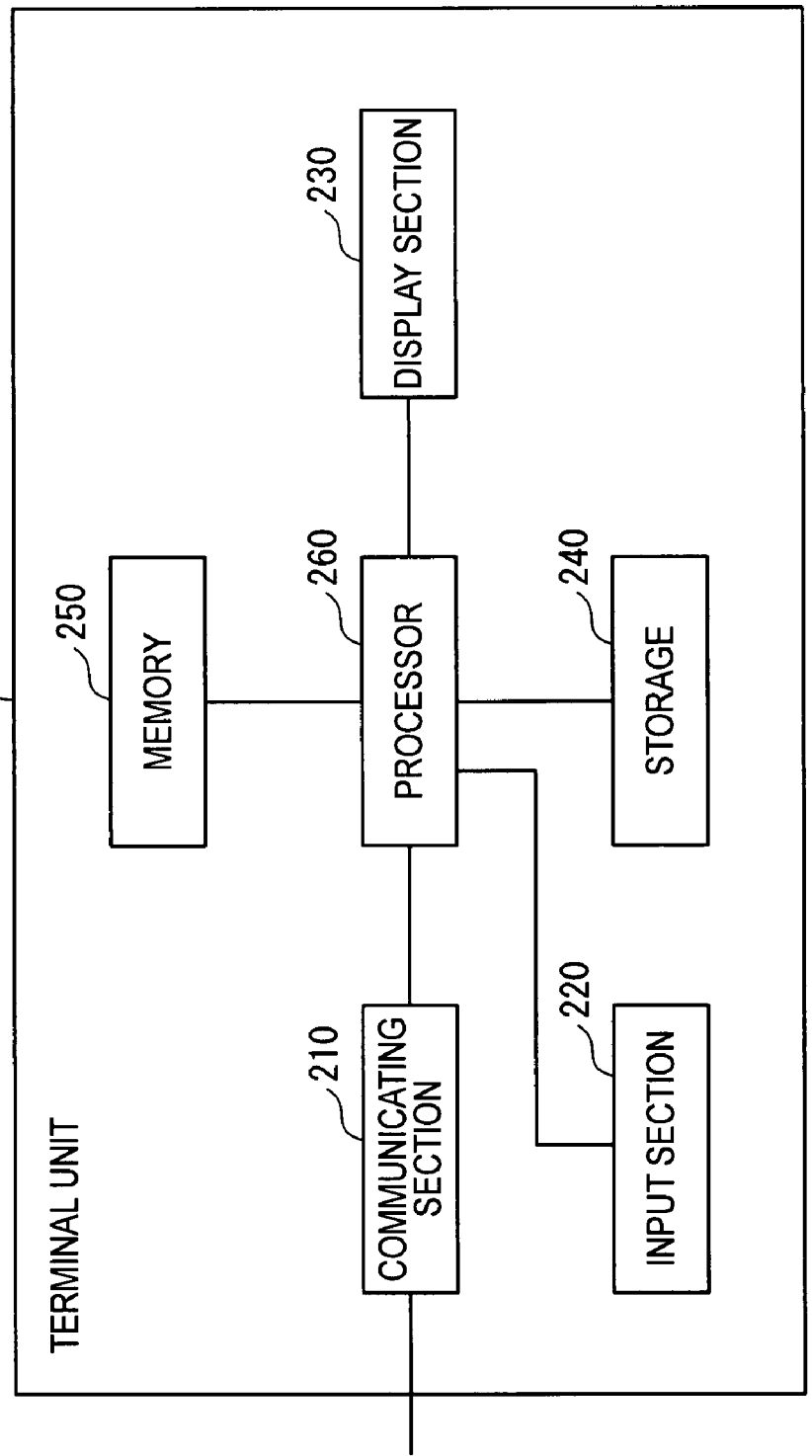
FIG. 2 is a block diagram schematically showing an overall architecture of a terminal unit.
Figure 3:
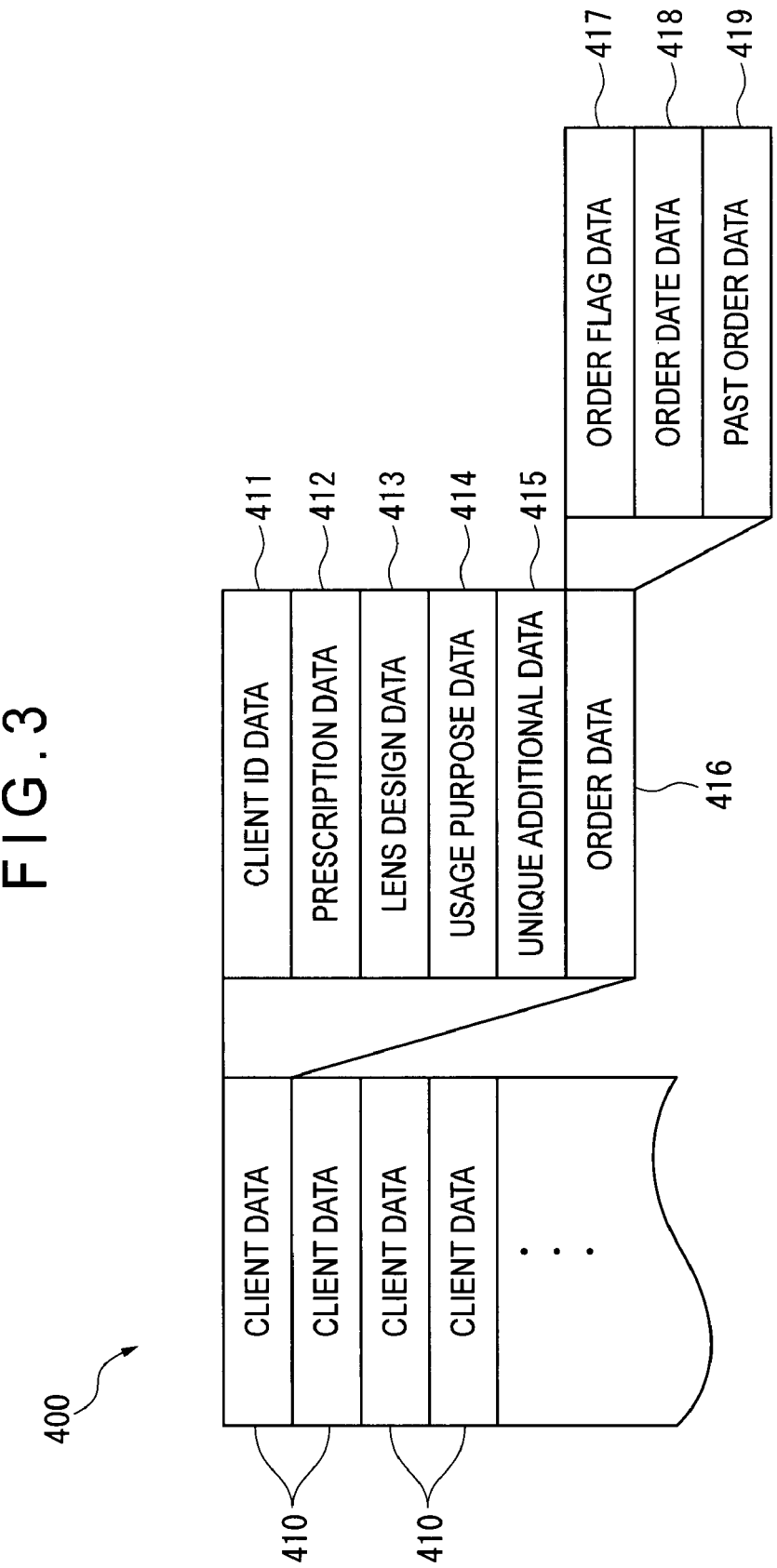
FIG. 3 schematically shows an architecture of a client data table stored in a storage of the terminal unit.
Figure 4:
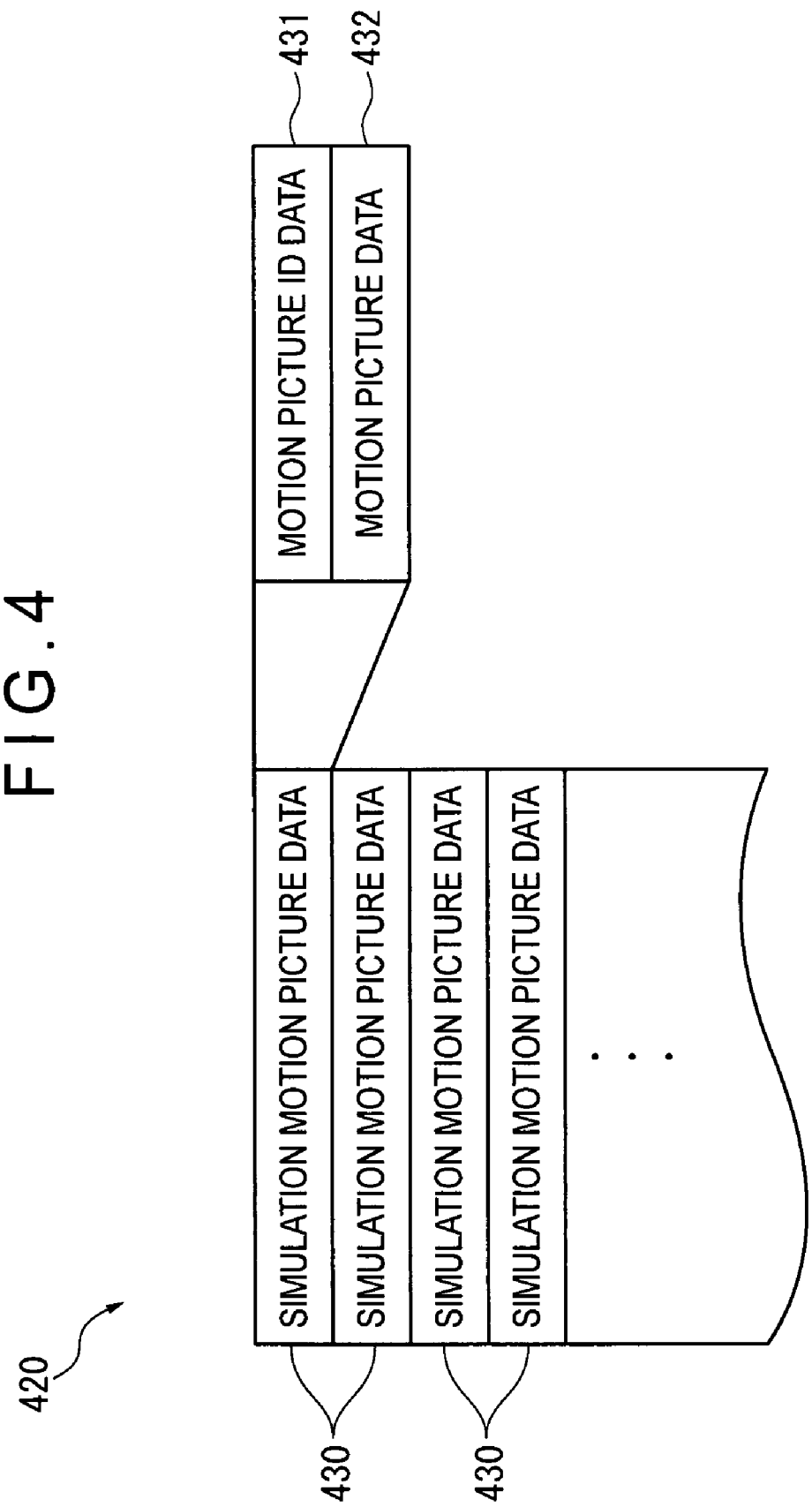
FIG. 4 shows an architecture of a simulation motion picture table stored in the storage of the terminal unit.
Figure 5:
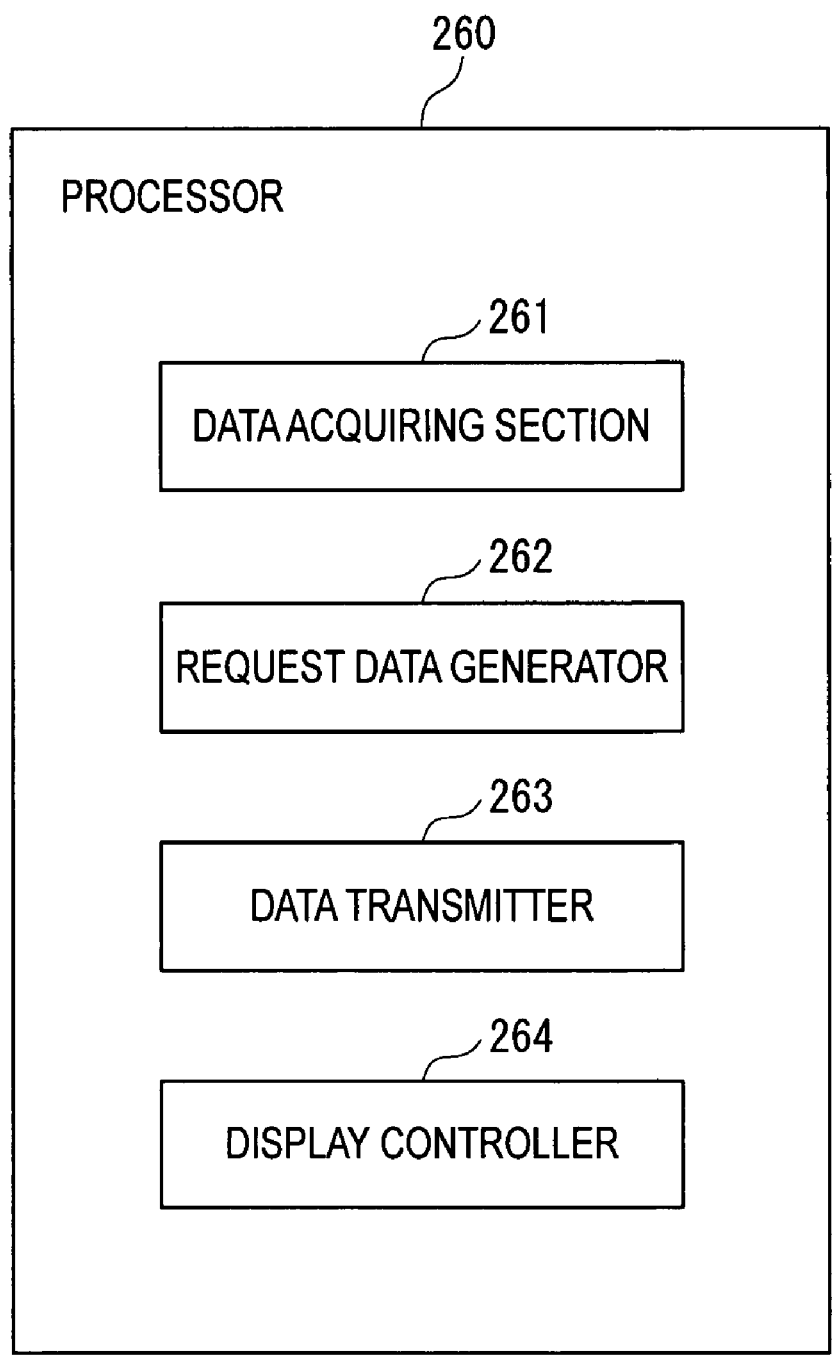
FIG. 5 is a block diagram schematically showing an overall architecture of a processor of the terminal unit.
Figure 6:
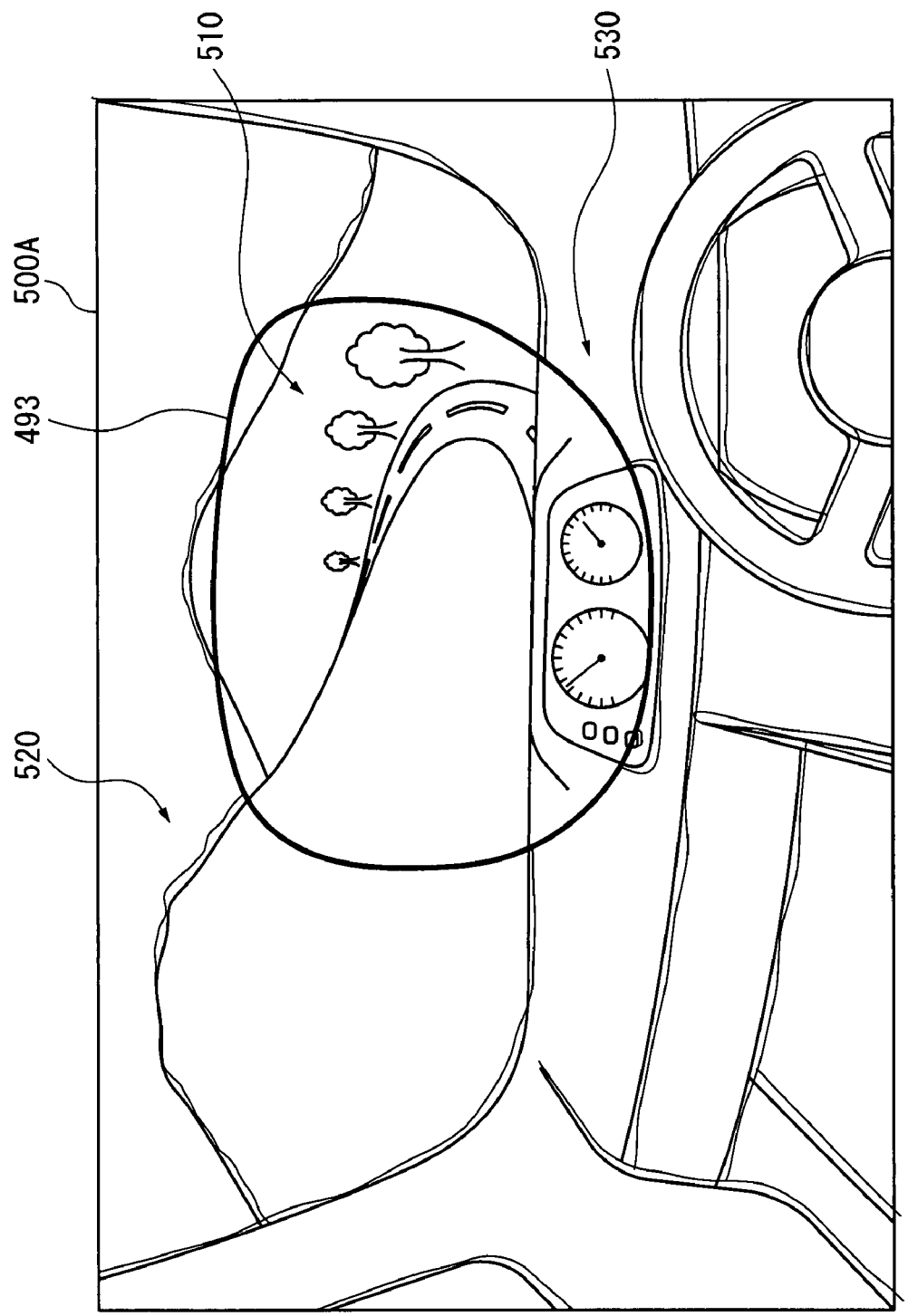
FIG. 6 shows simulation motion picture data for a far-middle lens.
Figure 7:
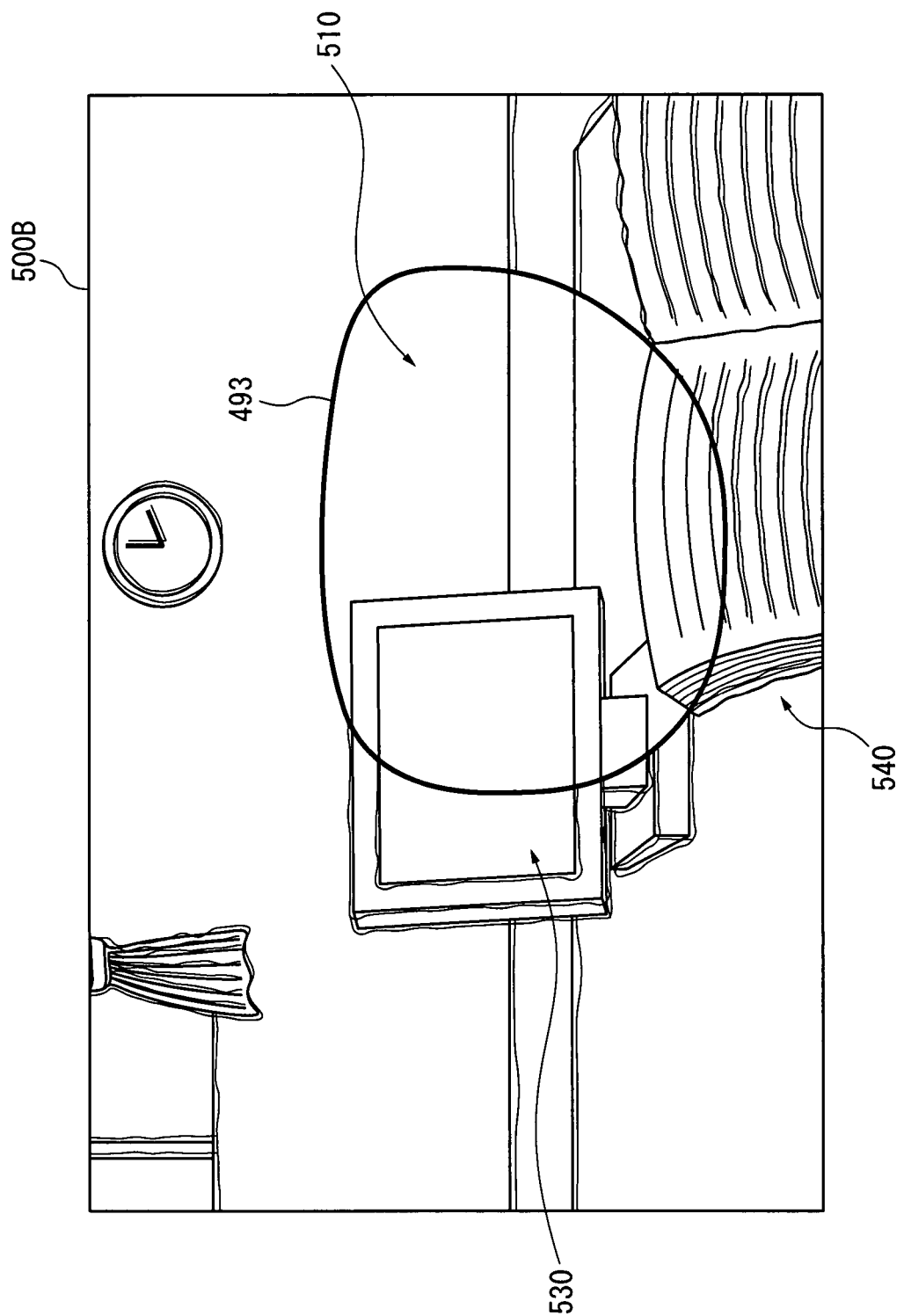
FIG. 7 shows simulation motion picture data for a middle-near lens.
Figure 8:
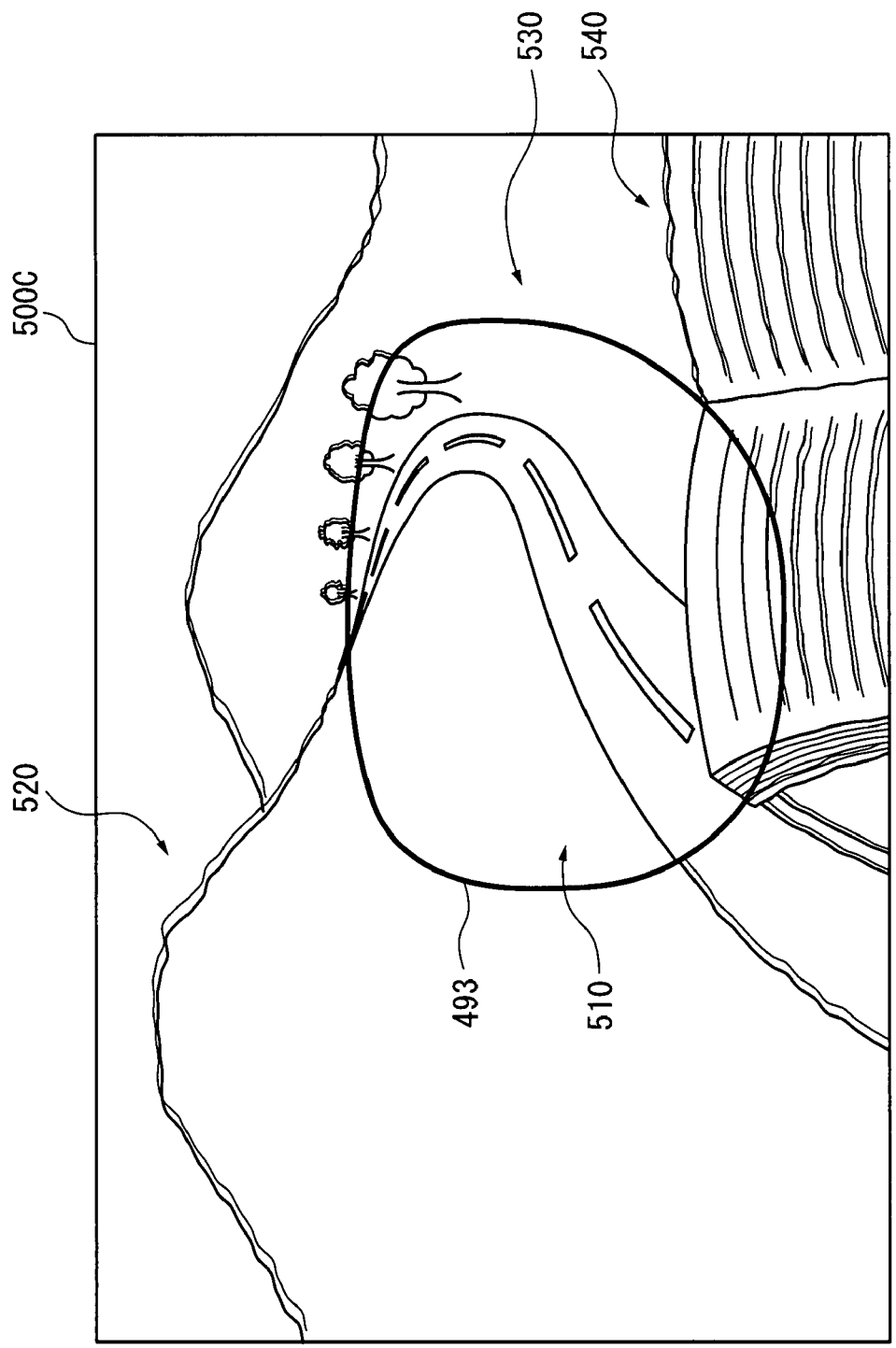
FIG. 8 shows simulation motion picture data for a far-near lens.
Figure 9:
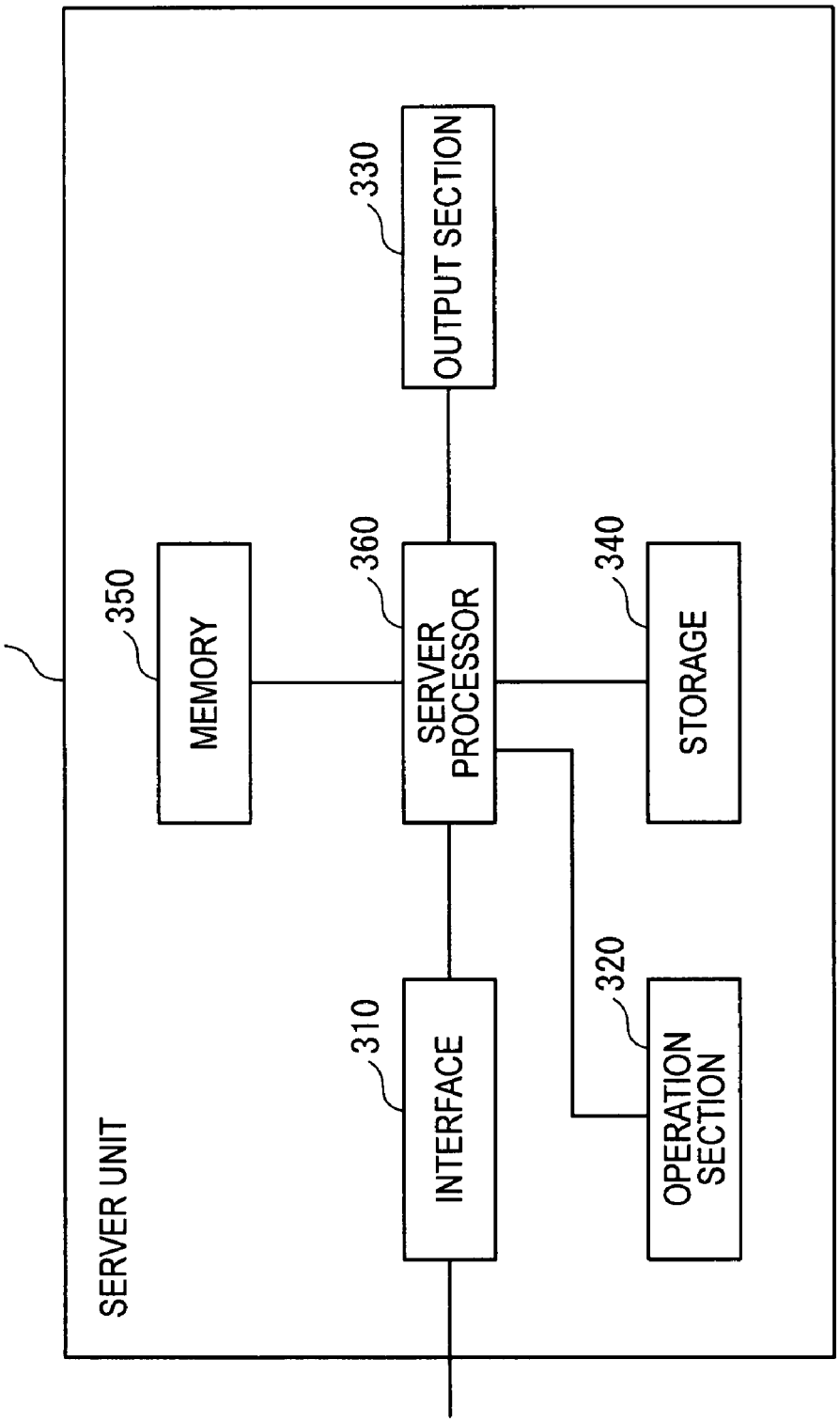
FIG. 9 is a block diagram schematically showing an overall architecture of a server unit.
Figure 10:
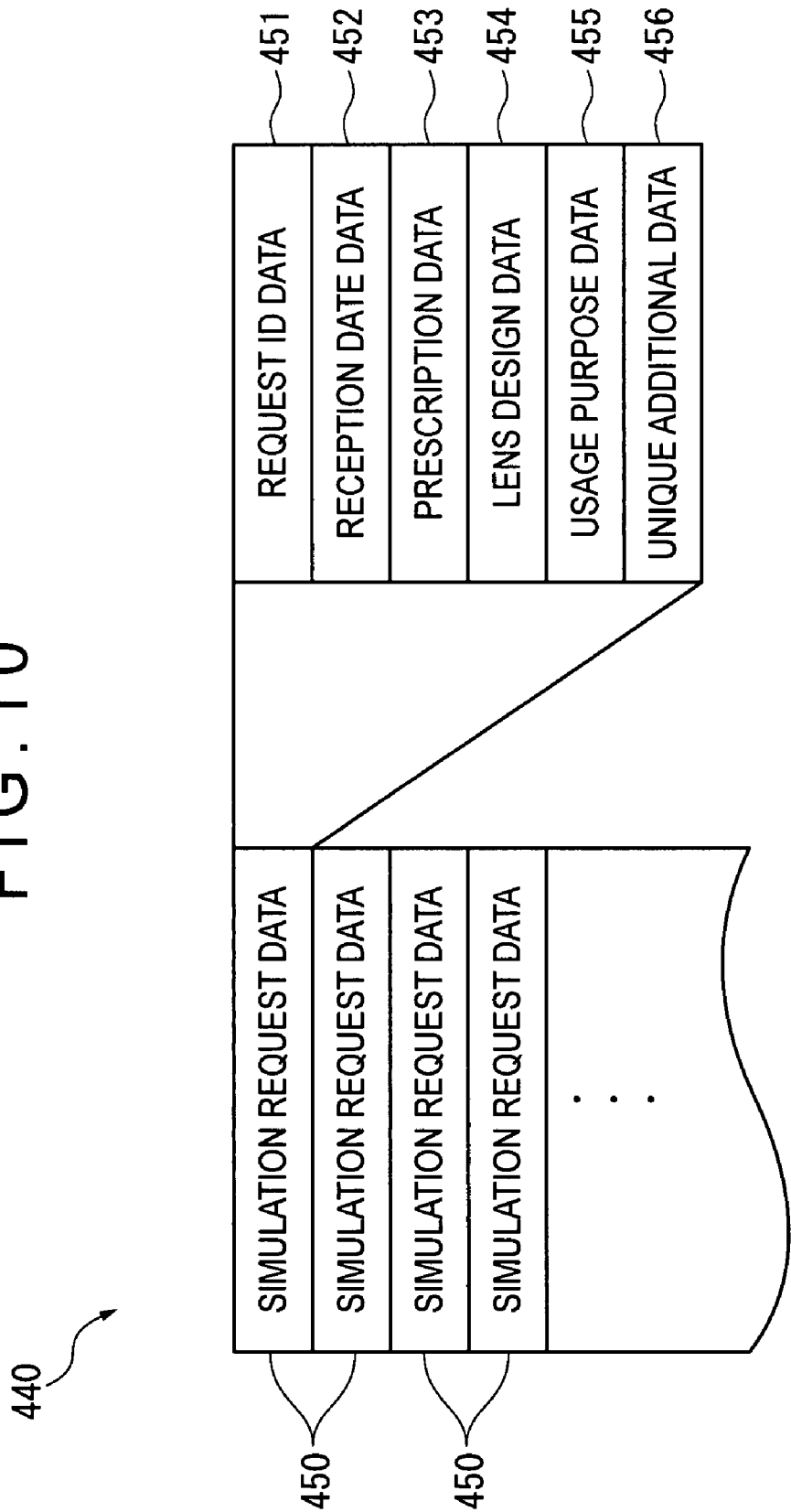
FIG. 10 schematically shows an architecture of a simulation request table stored in the storage of the server unit.
Figure 11:
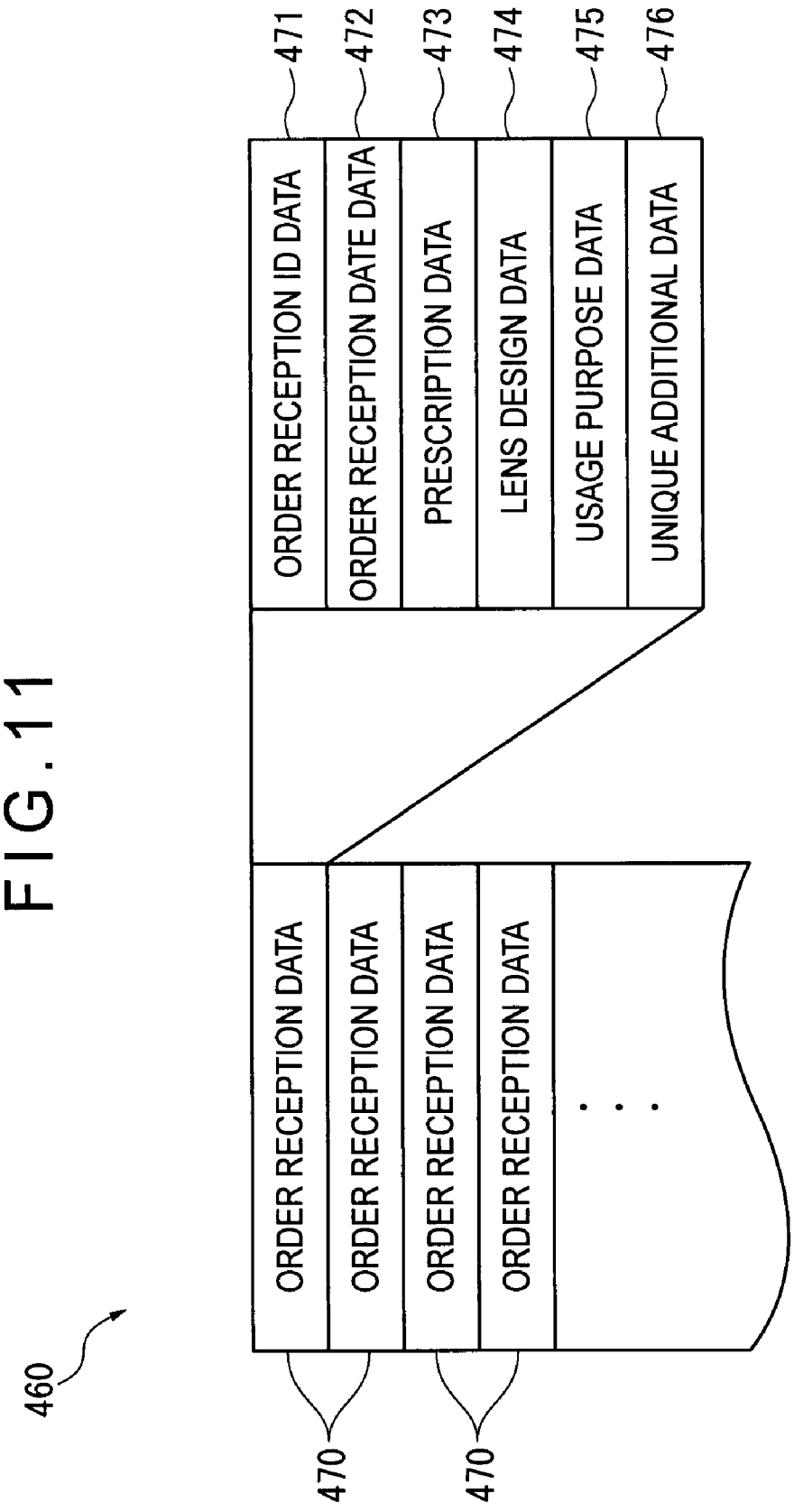
FIG. 11 schematically shows an architecture of an order reception table stored in the storage of the server unit.
Figure 12:
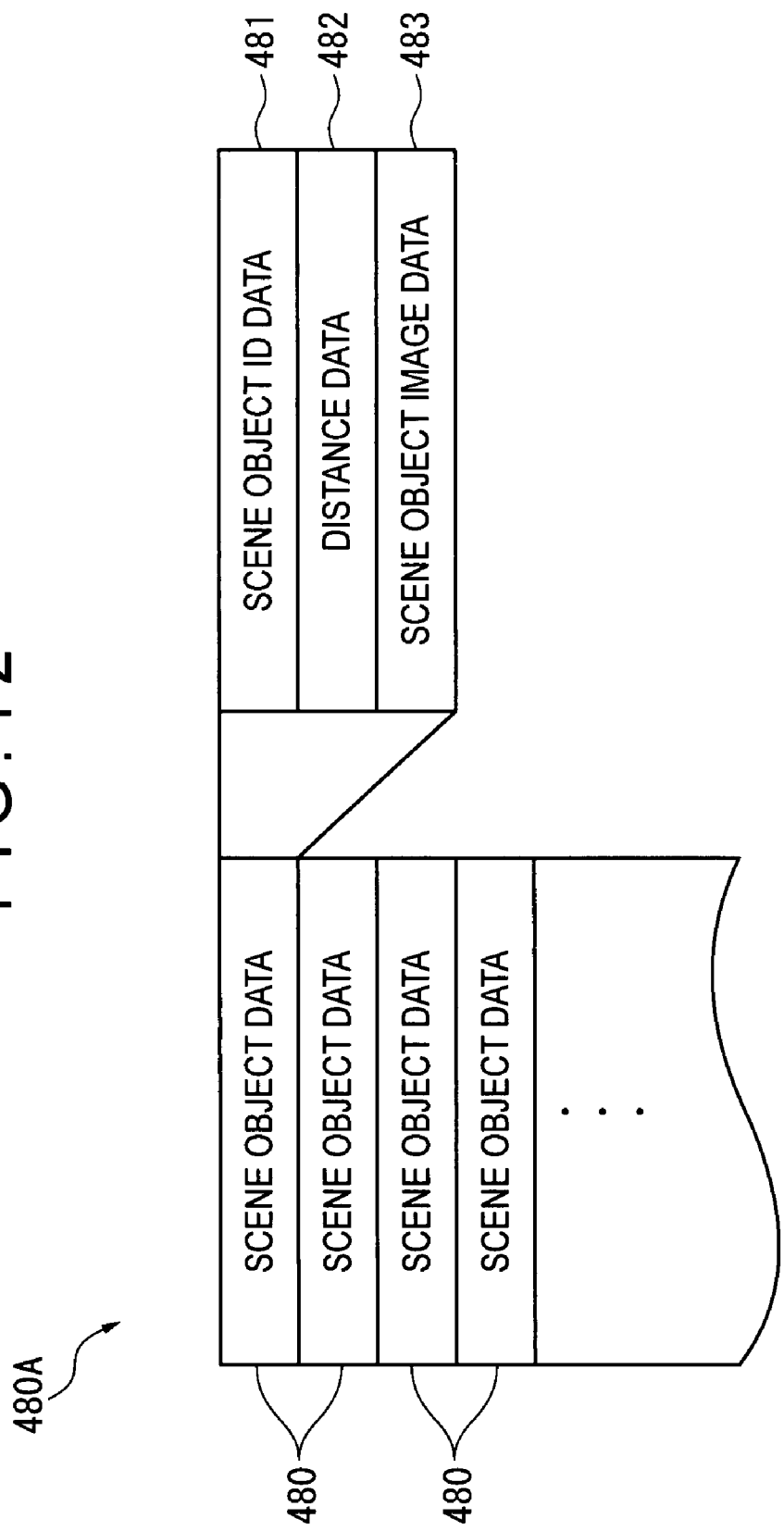
FIG. 12 schematically shows an architecture of a scene object table stored in the storage of the server unit.
Figure 13:
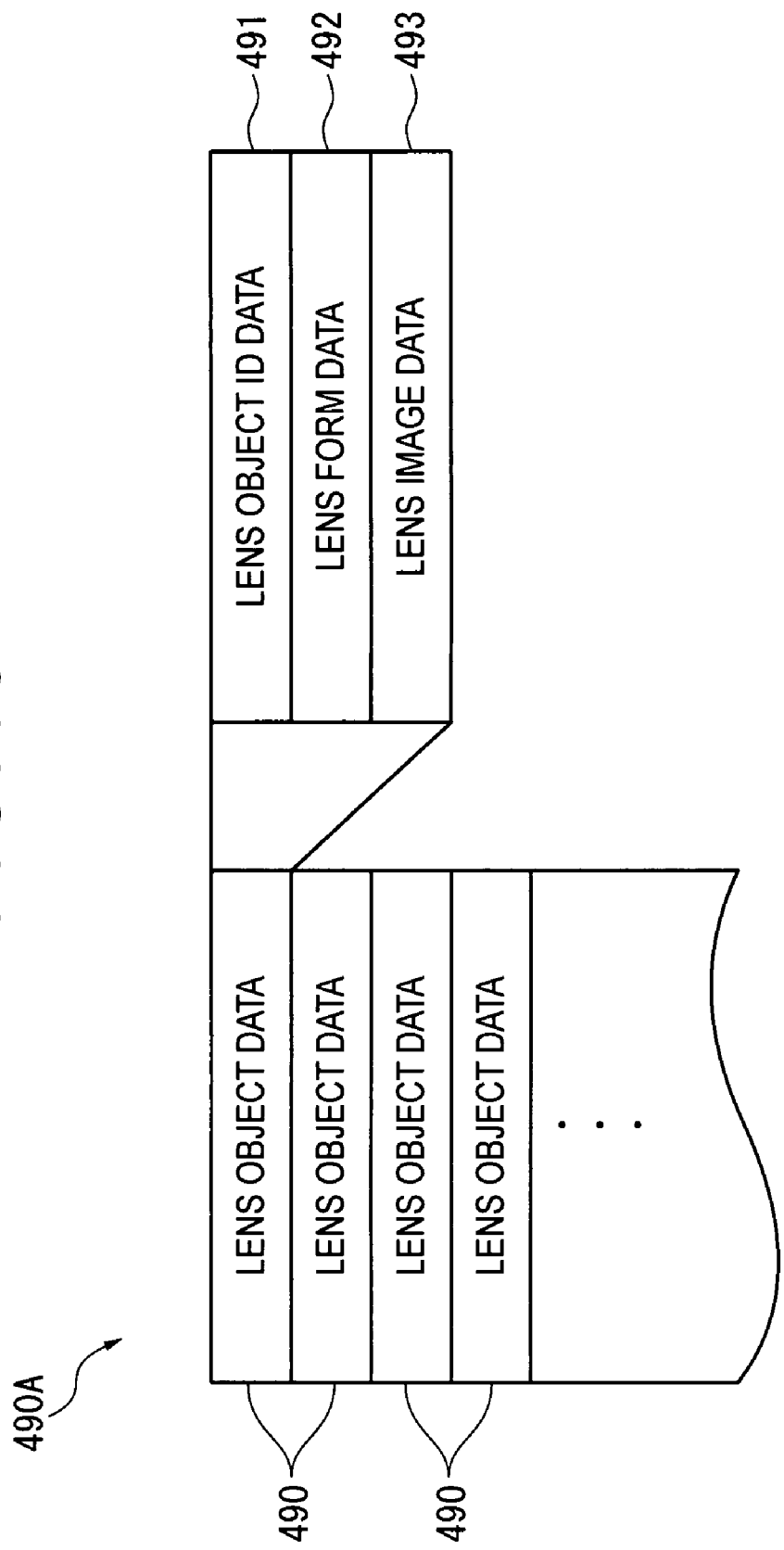
FIG. 13 schematically shows an architecture of a lens object table stored in the storage of the server unit.
Figure 14:
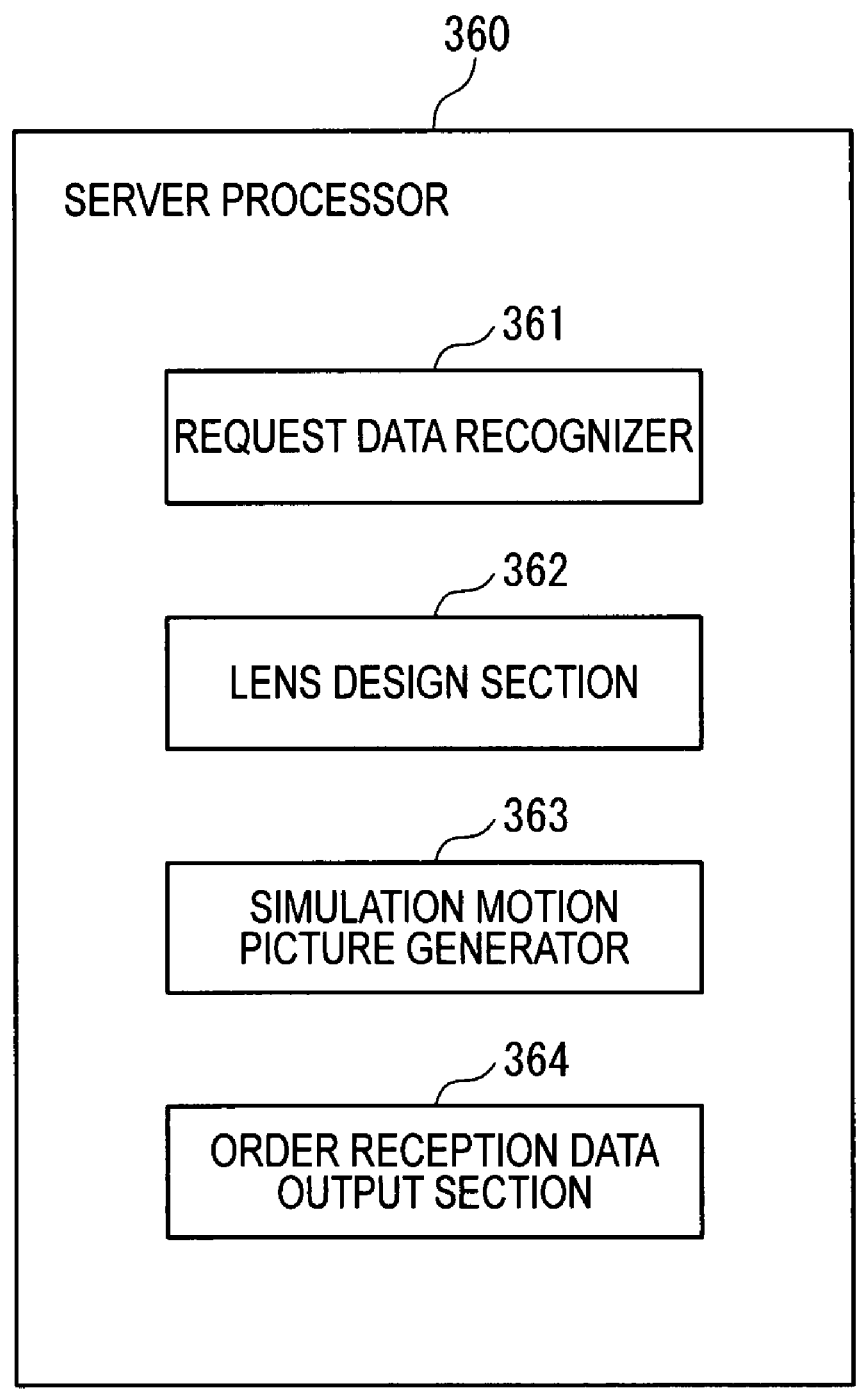
FIG. 14 is a block diagram schematically showing an overall architecture of a server processor of the server unit.

FIG. 2 is a block diagram schematically showing an overall architecture of a terminal unit. FIG. 3 schematically shows an architecture of a client data table stored in a storage of the terminal unit. FIG. 4 shows an architecture of a simulation motion picture table stored in the storage of the terminal unit. FIG. 5 is a block diagram schematically showing an overall architecture of a processor of the terminal unit. FIG. 6 shows simulation motion picture data for a far-middle lens. FIG. 7 shows simulation motion picture data for a middle-near lens. FIG. 8 shows simulation motion picture data for a far-near lens. FIG. 9 is a block diagram schematically showing an overall architecture of a server unit. FIG. 10 schematically shows an architecture of a simulation request table stored in the storage of the server unit. FIG. 11 schematically shows an architecture of an order reception table stored in the storage of the server unit. FIG. 12 schematically shows an architecture of a scene object table stored in the storage of the server unit. FIG. 13 schematically shows an architecture of a lens object table stored in the storage of the server unit. FIG. 14 is a block diagram schematically showing an overall architecture of a server processor of the server unit.

Architecture of Lens Order System

In FIG. 1, a lens order system 100 includes a network 110, a plurality of terminal units 200 and a server unit 300. The lens order system 100 is a communication system in which the terminal units 200 send data on an order for a lens such as a spectacles lens via the network 110 to the server unit 300, the server unit 300 receiving and processing the orders. In the exemplary embodiment, a lens order system for ordering a spectacles lens is exemplified, but the lens order system is also applicable for ordering another type of lens such as a contact lens. As the network 110, communication line networks such as the Internet based on a general protocol of TCP/IP and the like, an intranet, a LAN (Local Area Network) and a phone line can be exemplified.

Architecture of Terminal Unit

The terminal unit 200 is provided in a shop such as a spectacles lens shop and connected via the network 110 with the server unit 300. In the exemplary embodiment, the terminal unit 200 is a personal computer, but the terminal unit 200 is not limited thereto. The terminal unit 200 may be any device such as a portable phone, a TV device and a video device as long as the device can communicate via the network 110. As shown in FIG. 2, the terminal unit 200 includes a communicating section 210 as a terminal communicator, an input section 220, a display section 230 as a display, a storage 240, a memory 250, a processor 260 and the like.

The communicating section 210 is connected via the network 110 with the server unit 300 such that data can be transmitted therebetween. The communicating section 210 is connected with the processor 260 such that the communicating section 210 can transmit information via the network 110 with the server unit 300 under the control of the processor 260. The communicating section 210 outputs data acquired via the network 110 from the server unit 300 to the processor 260.

The input section 220 is a keyboard, a mouse and the like, the input section 220 having operation buttons or operation knobs (not shown) for an input operation. The input operation made on the operation buttons or the operation knobs includes operation setting of the server unit 300 and setting of the information to be stored in the terminal unit 200. In accordance with the input operation for a setting, the input section 220 outputs a signal corresponding to the setting to the processor 260 such that the setting is input. The input operation is not limited to an operation with the operation buttons or the operation knobs. The setting may be input by an operation on a touch panel provided on the display section 230 or by a voice input.

Under the control of the processor 260, the display section 230 displays a signal of image information input from the processor 260 on a display area (not shown). The image information includes: information acquired from the server unit 300; information stored in the storage 240; TV image information received by a TV receiver (not shown); and image information stored in a recording medium as an external device such as an optical disc, a magnetic disc or a memory card and read by a drive or a driver. The display section 230 may be a liquid crystal panel, an organic EL (Electro Luminescence) panel, a PDP (Plasma Display Panel), a CRT (Cathode-Ray Tube), an FED (Field Emission Display), an electrophoretic display panel or the like.

The storage 240 readably stores a client data table 400 (FIG. 3), a simulation motion picture table 420 (FIG. 4), server connection data and the like. The storage 240 includes a client data storage area (not shown) for storing the client data table 400, a motion picture storage area (not shown) for storing the simulation motion picture table 420, a connection destination storage area for storing the server connection data is stored and the like. Note that the storage 240 herein includes the above-described three storage areas, but the architecture is not limited thereto. The storage 240 may have no storage area or may have an additional storage area to the above-described storage areas. The storage 240 may be a drive or a driver that readably stores data in a recording medium such as a HD (Hard Disk), a DVD (Digital Versatile Disc), an optical disc and a memory card.

The client data table 400 is a data table relating to an order of a lens from a client, a prescription for the lens and the like. As shown in FIG. 3, the client data table 400 is table-structured by plural pieces of client data 410, each structured by client ID data 411, prescription data 412, lens design data 413 (lens form design data), usage purpose data 414 (lens usage purpose data), unique additional data 415 and the like which are mutually associated in the client data 410. The prescription data 412, the lens design data 413, the usage purpose data 414 and the unique additional data 415 structure lens design detail data.

The client ID data 411 is unique information for identifying the client data 410, the client ID data 411 being set for each client data 410. The client data 410 may be a client number set for each client, client personal information such as a client name and the like.

The prescription data 412 is data on the vision or a lens prescription for the client of the client data 410 identified by the client ID data 411. The prescription data 412 includes vision data on the vision of the client, lens prescription data on a prescription for the lens to be designed and the like.

The vision data includes data on the vision of the client such as the visual acuity of his naked eyes and the presence of astigmatism. The lens prescription data includes data on a spherical power, an astigmatic power, an astigmatic axis, an addition power, a prismatic power, an inset amount for near vision and the like of a lens.

The lens design data 413 is data on a form of a lens. The lens design data 413 includes data relating to information on a lens material (e.g. information on the refractive index of the lens), a design type, a sale name, a design parameters such as progressive band length and the like, a lens shape model, a size of the lens model, a frame form of a spectacles lens and the like.

The usage purpose data 414 is data on a purpose for which the lens is used. The usage purpose data 414 includes usage situation data on a situation where the lens is used, usage distance data on a distance from a lens user to a to-be-seen object and the like. A usage situations is stored as usage situation data, which includes deskwork, using a personal computer, housework, playing golf, fishing, driving, reading, writing, sewing and the like. The usage distance data is a near distance use when the distance from the lens to the object is equal to or longer than 50 cm, a middle-near distance use when the distance is equal to or shorter than 3 m, a middle distance use when the distance is between 1 to 5 m and a long distance use when the distance is equal to or longer than 5 m, where at least one of these categories in accordance with the distance of the usage purpose by the client and stored as the usage distance data.

The usage purpose data 414 is not limited to the above architecture. For example, data on a hobby or an occupation of the client or numeric data specifically showing a distance from the lens to the to-be-seen object may be stored as the usage distance data, or the usage purpose data 414 may only include either one of the usage situation data and the usage distance data.

The unique additional data 415 includes unique data of a client who uses the lens such as data on motions of the eyeballs or the head of the client, data on convergence force and the like. When the unique additional data 415 is not set, the numeral "0" indicating that no setting has been input may be stored as an initial value.

Order data 416 is data on a lens order status. The order data 416 is structured by order flag data 417, order date data 418, past order data 419 and the like associated as one piece of data.

The order flag data 417 is flag data indicating whether or not the client has ordered a lens. When the client has ordered a lens, for example, "1" indicating that the lens has been ordered is stored. When the client has not ordered a lens, for example, "0" indicating that no lens has been ordered is stored.

The order date data 418 is data on a lens ordered date when the data indicating that the lens has been ordered (e.g. "1") is stored in the order flag data 417. Note that when "0" indicating that no lens has been ordered is stored in the order flag data 417, no data may not be stored in the order date data 418.

The past order data 419 is data on an order history of the client identified by the client ID data 411. The past order data 419 may be associated with, as well as the lens order date in the past, the prescription data 412, the lens design data 413, the usage purpose data 414 and the unique additional data 415 of the lens ordered in the past, and the like. In addition, design data (detailed design lens data of the lens manufactured based on the above-described data in the past) may be stored.

The simulation motion picture table 420 includes plural pieces of simulation motion picture data 430 showing in a motion picture the lens user's vision through the designed lens. The simulation motion picture data 430 is structured by motion picture ID data 431 and motion picture data 432 associated as one piece of data.

The motion picture ID data 431 is unique information for identifying the simulation motion picture data 430, the motion picture ID data 431 being set for each simulation motion picture data 430. The motion picture ID data 431 includes data such as an ID number for identifying the simulation motion picture data 430, which is associated with the client ID data 411. Accordingly, it is possible to easily recognize which motion picture data 432 of the simulation motion picture data 430 corresponds to which lens ordered by the client.

The motion picture data 432 includes a motion picture showing the actual vision of the lens user through the lens designed based on the prescription data 412, the lens design data 413, the usage purpose data 414 and the unique additional data 415 of the client data 410 identified by the client ID data 411 that is associated with the motion picture ID data 431.

Server destination data (not shown) stored in the connection destination storage area of the storage 240 includes information on the server unit 300 that transmits data via the network 110. The server destination data is structured by, for example, server name data, address data, server user data, password data and the like associated as one piece of data. The sever name data is data on a name of the server unit 300 that is a connection destination. The address data is data on an IP address, a domain or the like of the server unit 300. The server user data is, for example, ID data that is stored in the server unit 300 and used for transmitting data with the server unit 300, the ID data being set for each terminal unit 200, a shop or the like. The password data is data on a password for the server user data for preventing a false use by a third party.

The memory 250 readably stores setting details input by the input section 220, audio information, image information and the like. The memory 250 also stores programs running on an OS (Operating System) operating the whole terminal unit 200. The memory 250 may include a drive or a driver that readably stores data in a recording medium such as a HD, a DVD, an optical disc and the like.

The processor 260 includes input/output ports (not shown) such as a communication port connected with the communicating section 210, a key input port connected with the input section 220, a display port connected with the display section 230, a storage port connected with the storage 240, a memory port connected with the memory 250 and the like. As shown in FIG. 5, the processor 260 includes as programs a data acquiring section 261, a request data generator 262 also functioning as an order section, a data transmitter 263, a display controller 264 and the like.

The data acquiring section 261 recognizes an input signal generated by an input operation made by the user on the input section 220, the data acquiring section 261 also recognizing setting detail data based on the input signal. The setting detail data includes a client data setting request data for setting the client data 410, a reproduction request data for reproducing the simulation motion picture data 430, transmission request data for transmitting data from the server unit 300 and other setting data.

Based on the client data setting request data recognized by the data acquiring section 261, the request data generator 262 sets the client ID data 411, the prescription data 412, the lens design data 413, the usage purpose data 414, the unique additional data 415 and the order data 416 to generate the client data 410.

Specifically, when the client data 410 is created for a new client, the request data generator 262 creates new client ID data 411 different from the client ID data 411 of the client data 410 of the existing clients and sets the prescription data 412, the lens design data 413, the usage purpose data 414 and the unique additional data 415, in which the data 412 to 415 are associated with each other.

On the other hand, when there is the client ID data 411 that identifies the existing client (e.g. when the client has used the lens order system 100), the request data generator 262 recognizes the client data 410 identified by the client ID data 411 and the past order data 419 of the client data 410. Based on the past order data 419, the request data generator 262 recognizes the prescription data 412, the lens design data 413, the usage purpose data 414 and the unique additional data 415 of the lens ordered last time and sets data to be changed based on the client data setting request data set by an input on the data acquiring section 261. In the exemplary embodiment, the request data generator 262 that recognizes the past order data 419 is exemplified, but the request data generator 262 may be adapted to re-set the prescription data 412, the lens design data 413, the usage purpose data 414 and the unique additional data 415.

When order request data for ordering a lens is included in the client data setting request data recognized by the data acquiring section 261, the request data generator 262 stores, for example, "1" in the order flag data 417 of the order data 416 of the client data 410 and data on the date when the client data setting request data is input in the order date data 418. On the other hand, when the request data generator 262 recognizes that motion picture creation data for requesting a creation of the simulation motion picture data is stored in the client data setting request data recognized by the data acquiring section 261, the request data generator 262 stores, for example, "0" in the order flag data 417.

When the data acquiring section 261 recognizes transmission request data, the data transmitter 263 transmits data via the communicating section 210 with the server unit 300.

Specifically, when the data acquiring section 261 recognizes the transmission request data for requesting that the client data 410 identified by a predetermined client ID data 411 be sent, the data transmitter 263 controls the communicating section 210 to send the client data 410 of the client ID data 411 to the server unit 300. At the same time, based on the server destination data stored in the storage 240, the data transmitter 263 is operated such that the client data 410 is sent to a predetermined server unit 300. The data transmitter 263 sends the server unit 300 the client data 410 and data identifying the terminal unit 200 (e.g. the server user data and the password data of the server destination data) which are associated with the client data 410.

The data transmitter 263 controls the communicating section 210 to receive the simulation motion picture data 430 sent from the server unit 300. The received simulation motion picture data 430 is readably stored in the simulation motion picture table 420 of the storage 240.

When the display controller 264 recognizes a request for inputting the client data setting request data based on setting input data recognized by the data acquiring section 261, the display controller 264 is operated such that an input setting screen for prompting an input of the client data setting request data is displayed on a display area (not shown) of the display section 230. Although not specifically shown, the input setting screen includes a data display frame for displaying the client ID data 411, the prescription data 412, the lens design data 413, the usage purpose data 414, the unique additional data 415 and the order data 416 of the client data 410 and the like, a send button for sending the client data 410 to the server unit 300 as the request data, a reproduction button for reproducing the simulation motion picture data 430 and the like.

When the data acquiring section 261 recognizes that the reproduction request data for requesting a reproduction of the simulation motion picture data 430 is input, the display controller 264 is operated such that the simulation motion picture data 430 is recognized and the motion picture data 432 is displayed on the display area of the display.

Specifically, the display controller 264 is operated such that, for example, a motion picture reproduction button for reproducing the simulation motion picture data 430 is displayed on a portion of the above-described input setting screen. When the data acquiring section 261 recognizes that the motion picture reproduction button is selected (e.g. clicked), the display controller 264 recognizes the simulation motion picture data 430 including the motion picture ID data 431 associated with the client ID data 411 of the client data 410. The display controller 264 recognizes the motion picture data 432 of the simulation motion picture data 430 and controls such that a simulation motion picture (FIGS. 6 to 8) is displayed on the display area of the display section 230.

Now, the simulation motion picture displayed on the display area of the display section 230 will be described. The simulation motion picture simulates the actual vision of the lens user of a scene, a person, an object and the like observed through the lens designed based on the data stored in the client data 410. In the exemplary embodiment, FIGS. 6 to 8 respectively exemplify a far-middle lens simulation motion picture 500A for a middle to far distance between the lens and the to-be-seen object, a middle-near lens simulation motion picture 500B for a near to middle distance between the lens and the to-be-seen object and a far-near lens simulation motion picture 500C for a near to far distance between the lens and the to-be-seen object. However, the architecture is not limited thereto. More simulation motion pictures corresponding to actual distances from the lens to the to-be-seen object may be used.

As shown in FIG. 6, in the far-middle lens simulation motion picture 500A, far distance image data 520 and middle distance image data 530 are combined to form composition image data on which lens image data 493 is superposed and moved. As shown in FIG. 7, in the middle-near lens simulation motion picture 500B, the lens image data 493 is superposed and moved on composition image data combining the middle distance image data 530 and near distance image data 540. As shown in FIG. 8, in the far-near lens simulation motion picture 500C, the lens image data 493 is superposed and moved on composition image data combining the far distance image data 520, the middle distance image data 530 and the near distance image data 540.

In each simulation motion picture 500A, 500B, 500C, the lens image data 493 shows a lens form corresponding to the lens design data 413 of the client data 410. The far distance image data 520 shows an object at a long distance from the lens (e.g. 10 m or more). The middle distance image data 530 shows an object at a middle distance from the lens (e.g. 50 cm to 2 m). The near distance image data 540 shows an object at a short distance from the lens (e.g. 50 cm or less).

Based on the prescription data 412 and the unique additional data 415 of the client data 410, the far distance image data 520, the middle distance image data 530 and the near distance image data 540 are each image-processed to show the actual vision of a client when the client sees each image without wearing the lens from a predetermined distance. The superposing portions 510 of the lens image data 493 and the far distance image data 520, the middle distance image data 530 and the near distance image data 540 are each image-processed to show the actual vision of the client when the client sees the far distance image data 520, the middle distance image data 530 and the near distance image data 540 with the lens designed based on the prescription data 412, the lens design data 413, the usage purpose data 414, the unique additional data 415 and the like.

Architecture of Server Unit

As described above, the server unit 300 is provided in a communicable manner with the terminal unit 200 via the network 110. The server unit 300 is provided in a premise of a manufacturer of a lens such as a spectacles lens. The server unit 300 receives order data of a spectacles lens ordered from the terminal unit 200 and processes the received order. The server unit 300 designs a lens based on data input from the terminal unit 200, generates the simulation motion picture data 430 on which the lens image data corresponding to the lens is superposed and sends the generated data to the terminal unit 200. As shown in FIG. 9, the server unit 300 includes an interface 310 as a server communicator, an operation section 320, an output section 330, a storage 340, a memory 350 and a server processor 360.

The interface 310 is connected via the network 110 with the terminal unit 200. The interface 310 is electrically connected with the server processor 360. The interface 310 performs a predetermined input interface processing for a server signal input via the network 110 and outputs a processing server signal to the server processor 360. When the processing server signal to be sent from the server processor 360 to the terminal unit 200 is input to the interface 310, the interface 310 performs a predetermined output interface processing for the input processing server signal and outputs a server signal via the network 110 to the terminal unit 200.

Similarly to the input section 220 of the terminal unit 200, the operation section 320 is a keyboard or a mouse for example, the input section 220 having operation buttons or operation knobs (not shown) for an input operation. The input operation made on the operation buttons or the operation knobs includes operation setting of the server unit 300, setting of the information to be stored in the storage 340 and update setting of the information stored in the storage 340. In accordance with the input operation for a setting, the operation section 320 outputs a signal corresponding to the setting to the server processor 360 such that the setting is input. The input operation is not limited to an operation on the operation buttons or the operation knobs. The setting may be input by an operation on a touch panel provided on the display of the output section 330 or a voice input.

The output section 330 includes the display that is controlled by the server processor 360 and displays a signal of image data from the server processor 360. Similarly to the display section 230 of the terminal unit 200, the display may be a liquid crystal panel, an organic EL panel, a PDP, a CRT, an FED and an electrophoretic display panel. Although the display is used as the output section 330, a printer that outputs predetermined data print-out, an audio outputting section that outputs data with sound or the like may be alternatively employed.

The storage 340 includes a simulation request storage area for storing the simulation request table 440 relating to a request for creating the simulation motion picture data 430, an order reception storage area for storing order reception table 460 relating to an order reception, a scene object storage area for storing a scene object table relating to an image of a simulation motion picture, a lens object storage area for storing a lens object table and the like. The storage 340 may be a drive or a driver that readably stores data in a recording medium such as a HD, a DVD, an optical disc, a memory card and the like.

The simulation request table 440 stored in the storage 340 is a data table relating to a request for creating the simulation motion picture data sent from the terminal unit 200. As shown in FIG. 10, the simulation request table 440 is table-structured by plural pieces of simulation request data 450, each having request ID data 451, reception date data 452, prescription data 453, lens design data 454 (lens form design data), usage purpose data 455 (lens usage purpose data), unique additional data 456 and the like associated as one piece of data. The simulation request data 450 is generated based on the client data 410 sent from the terminal unit 200, of which prescription data 453, lens design data 454, usage purpose data 455 and unique additional data 456 store substantially the same data as the prescription data 412 of, the lens design data 413, the usage purpose data 414 and the unique additional data 415 of the client data 410.

The request ID data 451 is unique data for identifying the simulation request data 450, which is associated with the client ID data 411. Specifically, the request ID data 451 stores, for example, the client ID data 411 of the client data 410, the server user data of the terminal unit 200 (a sender) and the like.

The reception date data 452 is data on a date when the simulation request data 450 identified by the request ID data 451 is created. Specifically, the reception date data 452 stores a date when the server unit 300 receives, for example, the client data 410 as a creation basis.

The order reception table 460 is a data table relating to a receipt of a lens order sent from the terminal unit 200. As shown in FIG. 11, the order reception table 460 is table-structured by plural pieces of order reception data 470, each having order reception ID data 471, order reception date data 472, prescription data 473, lens design data 474 as lens form design data, usage purpose data 475 as lens usage purpose data, unique additional data and the like associated as one piece of data. Similarly to the simulation request ID data 450, the order reception data 470 is generated based on the client data 410 sent from the terminal unit 200, of which prescription data 473, lens design data 474, usage purpose data 475 and unique additional data 476 store substantially the same data as the prescription data 412, the lens design data 413, the usage purpose data 414 and the unique additional data 415 of the client data 410.

The order reception ID data 471 is unique data for identifying the order reception data 470 and is associated with the client ID data 411. Specifically, the order reception ID data 471 includes, for example, the client ID data 411 of the client data 410, the server user data of the terminal unit 200 (a sender) and the like.

The order reception date data 472 is data on a date when the order reception data 470 identified by the order reception ID data 471 is generated. Specifically, the order reception date data 472 includes a date when the server unit 300 receives, for example, the client data 410 as a creation basis.

A scene object table 480A is a data table relating to the far distance image data 520, the middle distance image data 530 and the near distance image data 540 which form the above-described simulation motion picture data 430. As shown in FIG. 12, the scene object table 480A is table-structured by plural pieces of scene object data 480, each having scene object ID data 481, distance data 482, scene object image data 483 as image data and the like associated as one piece of data.

The scene object ID data 481 is unique data for identifying the scene object data 480 and is set for each scene object data 480.

The distance data 482 is data on a distance from the lens to the image data (the to-be-seen object) of the scene object data 480 identified by the scene object ID data 481. Specifically, the distance data 482 includes data on a distance from the lens to the to-be-seen object. Note that the distance data 482 may be classified data such as, for instance, far distance, middle distance and near distance in which the distance from the lens to the to-be-seen object is classified based on a predetermined distance is stored. Alternatively, values representing the distance from the lens to the to-be-seen object may be stored as the distance data 482.

The scene object image data 483 stores the image data 520, 530, 540 forming the motion picture data 432 of the simulation motion picture data 430.

A lens object table 490A is a data table storing the lens image data 493 (image data) forming the above-described simulation motion picture data 430. As shown in FIG. 13, the lens object table 490A is table-structured by plural pieces of lens object data 490, each having lens object ID data 491, lens form data 492, the lens image data 493 and the like associated as one piece of data.

The lens object ID data 491 is unique data for identifying the lens object data 490 is set for each lens object data 490.

The lens form data 492 is data on a form of a lens. The lens form data 492 includes data on the refractive index or the Abbe number of a lens material, coordinate value data of refracting surfaces of a lens (anterior and posterior surfaces), thickness data such as a center thickness of the lens, a lens shape model, a size of the lens shape model, a frame form of a spectacles lens and the like. Additionally, data on refracting on points on the lens (such as refracting power, a prism effect and the like) may be included.

The lens image data 493 includes the lens image data 493 forming the motion picture data 432 of the simulation motion picture data 430.

The memory 350 readably stores settings, audio information, image information and the like which are input with the operation section 320. The memory 350 also stores programs running on an OS (Operating System) operating the whole server unit 300. The memory 350 may include a drive or a driver that readably stores data in a recording medium such as a HD, a DVD, an optical disc and the like in a readable manner.

As shown in FIG. 14, the server processor 360 includes, as programs stored in the memory 350, a request data recognizer 361 also functioning as a data recognizer and an order reception section, a lens design section 362, a simulation motion picture generator 363 also functioning as an image data recognizer and an image processor, an order reception data output section 364 and the like.

The request data recognizer 361 controls the interface 310, receives data (e.g. the client data 410) sent from the terminal unit 200 and recognizes the received data. When recognizing the client data 410 sent from the terminal unit 200, the request data recognizer 361 recognizes the order flag data 417 of the order data 416 of the client data 410.

When recognizing that data (e.g. "0") indicating no lens is ordered is stored in the order flag data 417, the request data recognizer 361 generates the simulation request data 450 based on the received client data 410 and readably stores the generated simulation request data 450 in the simulation request table 440 in the storage 340. At this time, the request data recognizer 361 stores the simulation request data 450 in the simulation request table 440 in an ascending order of the reception date data 452.

On the other hand, when recognizing that data (e.g. "1") indicating a lens is ordered is stored in the order flag data 417, the request data recognizer 361 generates the order reception data 470 based on the received client data 410 and readably stores the generated order reception data 470 in the order reception table 460 in the storage 340. At this time, the request data recognizer 361 stores the order reception data 470 in the order reception table 460 in an ascending order of the order reception date data 472.

The lens design section 362 designs a lens based on the simulation request data 450. Specifically, the lens design section 362 recognizes the prescription data 453, the lens design data 454, the usage purpose data 455 and the unique additional data 456 of the simulation request data 450.

The lens design section 362 designs the form of the lens based on the lens design data 454.

The lens design section 362 determines the distance characteristics of the lens based on the usage purpose data 455. Specifically, the lens design section 362 sets a ratio of areas of the lens for seeing a far-distanced, middle-distanced and near-distanced object. For example, when data indicating that the lens object is located at far to middle distance is stored (e.g. when playing golf, bird watching and the like are stored in the usage situation data or when data indicating that the lens is used in a distance of 50 cm and more is stored in the usage distance data), the lens design section 362 sets the distance characteristics such that the areas for seeing the far-distanced and middle-distanced object are large and the area for seeing the near-distanced object is small. On the other hand, when data indicating that the lens object is middle to near distanced is stored (e.g. when driving is stored in the usage situation data or when data indicating that the lens is used in a distance of 7 m or less is stored in the usage distance data), the lens design section 362 sets the distance characteristics such that the area for seeing the far-distanced object is small and the areas for seeing the middle-distanced and near-distanced object are large. Although the ratio of the areas can be flexibly designed and set in accordance with client's demands as described above, when a design type or a specific product name is sent in the lens design data (as design information) from a shop, the lens is designed in accordance with the sent data.

Subsequently, based on the prescription data 453 and the unique additional data 456, the lens design section 362 appropriately sets the thickness and weight of the lens and the curvature of the lens surface for each area for seeing the far, middle and near distanced objects.

The lens design section 362 readably stores the designed ratio of the areas, the thickness and weight of the lens, the curvature of the lens surface, the form of the lens and the like in the memory 350 or in the storage 340 as design lens data. When storing, the lens design section 362 associates the request ID data 451 of the simulation request data 450 with the design lens data. In the exemplary embodiment, the design lens data is initially created and then stored in the memory 350 in a readable manner, but the architecture is not limited thereto. For example, the design lens data may be initially added to the simulation request data 450 and then stored in the simulation request table 440.

The simulation motion picture generator 363 generates the simulation motion picture data 430 based on the simulation request data 450.

Specifically, based on the usage purpose data 455 of the simulation request data 450, the simulation motion picture generator 363 selects the scene object data 480 forming the motion picture data 432 from the scene object table 480A. For example, when data indicating that the lens object is located at far to middle distance is stored in the usage purpose data 455, the simulation motion picture generator 363 selects a predetermined number of pieces of scene object data 480 of which distance data 482 is far or middle distance. Note that the simulation motion picture generator 363 may select one piece of scene object data 480 for each distance. When a larger number than the predetermined number of scene object data 480 exist, a predetermined number of pieces of scene object data 480 with similar usage situations are selected based on the usage situation data of the usage purpose data 455. For example, when the usage situation data indicates golf-playing, the scene object data 480 of which scene object image data 483 is an image of golf course is selected by the predetermined number. Note that when a specific lens distance is stored in the distance data 482, the simulation motion picture generator 363 may select the distance data 482 having the nearest distance data 482 to the distance stored in the usage distance data of the usage purpose data 455.

The simulation motion picture generator 363 generates a composition image composed of the selected predetermined number of pieces of scene object data 480. At this time, for example, the scene object image data 483 with far-distance distance data 482 is disposed on an upper side of the composition image and the scene object image data 483 is disposed downward in the composition image as the distance data 482 approaches to a near distance.

Subsequently, the simulation motion picture generator 363 processes the image based on the prescription data 453 and the unique additional data 456 to show the lens user's vision of this composition image with naked eyes. For example, the simulation motion picture generator 363 image-processes the scene object image data 483 of the composition image based on the vision data of the prescription data 453 and the unique additional data 456 to display the image in a corresponding manner to the vision of the lens user with naked eyes, the astigmatic power, a heterophoria, an amplitude of convergence, where, for instance, the contour of the image is blurred, the contour is multiplied, the color runs and the scene object image data 483 is distorted. Herein, the simulation motion picture generator 363 image-processes each of the scene object image data 483 corresponding to each distance based on the distance data 482 of the scene object data 480 to show the vision of the object of the scene object image data 483 located at a position apart by a distance of the distance data 482. Accordingly, as shown in FIGS. 6 to 8, the scene object image data 483 disposed on the composition image is image-processed to a state in accordance with the vision of the lens user corresponding to each distance such that the far distance image data 520, the middle distance image data 530 and the near distance image data 540 are image-edited as shown in FIGS. 6 to 8.

Next, the simulation motion picture generator 363 selects the lens object data 490 from the lens object table 490A based on the lens design data 454. At this time, the simulation motion picture generator 363 selects the lens object data 490 having the lens form data 492 corresponding to the lens form, the lens size and the frame form stored in the lens design data 454.

As shown in FIGS. 6 to 8, the simulation motion picture generator 363 superposes the lens image data 493 of the selected lens object data 490 on the composition image.

Based on the design lens data generated by the lens design section 362, the simulation motion picture generator 363 image-processes the superposing portion 510 of the lens image data 493 and the composition image to show the lens user's vision of the object located at a position apart by the above-described distances through the lens designed by the lens design section 362. Based on the distance data 482 of the scene object data 480, the simulation motion picture generator 363 image-processes the superposing portion 510 of the lens image data 493 and the image data 520, 530, 540 corresponding to the distances to show the lens user's vision through the lens an object located at a position apart by the distance based on the distance data 482.

Further, the simulation motion picture generator 363 generates a composition motion picture on which the lens image data 493 is moved. Herein, in accordance with the movement of the lens image data 493, the superposing portion 510 with the composition image is sequentially image-processed to generate a composition motion picture in which the image data 520, 530, 540 out of the superposing portion 510 is restored to show the lens user's vision with naked eyes the object located at a position apart by the distance based on the distance data 482. Based on the design lens data, the prescription data 453 and the unique additional data 456, the simulation motion picture generator computes distortion of the image data generated by the movement of the lens image data 493 to reflect the distortion on the superposing portion 510.

The simulation motion picture generator 363 stores the generated composition motion picture as the motion picture data 432, associates the motion picture data 432 with the motion picture ID data 431 generated based on the request ID data 451 of the simulation request data 450 and generates the simulation motion picture data 430. The simulation motion picture generator 363 controls the interface 310 and sends the generated simulation motion picture data 430 to the terminal unit 200. Herein, based on the user server data sent from the terminal unit 200, the simulation motion picture generator 363 sends the simulation motion picture data 430 to the terminal unit 200 identified by the server user data.

When the order reception data output section 364 recognizes a request signal for outputting the order reception data 470 based on the operation input signal from the operation section 320 for example, the order reception data output section 364 controls the output section 330 to output the order reception data 470 stored in the order reception table 460. Note that the order reception data output section 364 may conduct a processing for outputting the order reception data 470 from the output section 330 at a predetermined time interval.

Operation of Lens Order System

Figure 15:
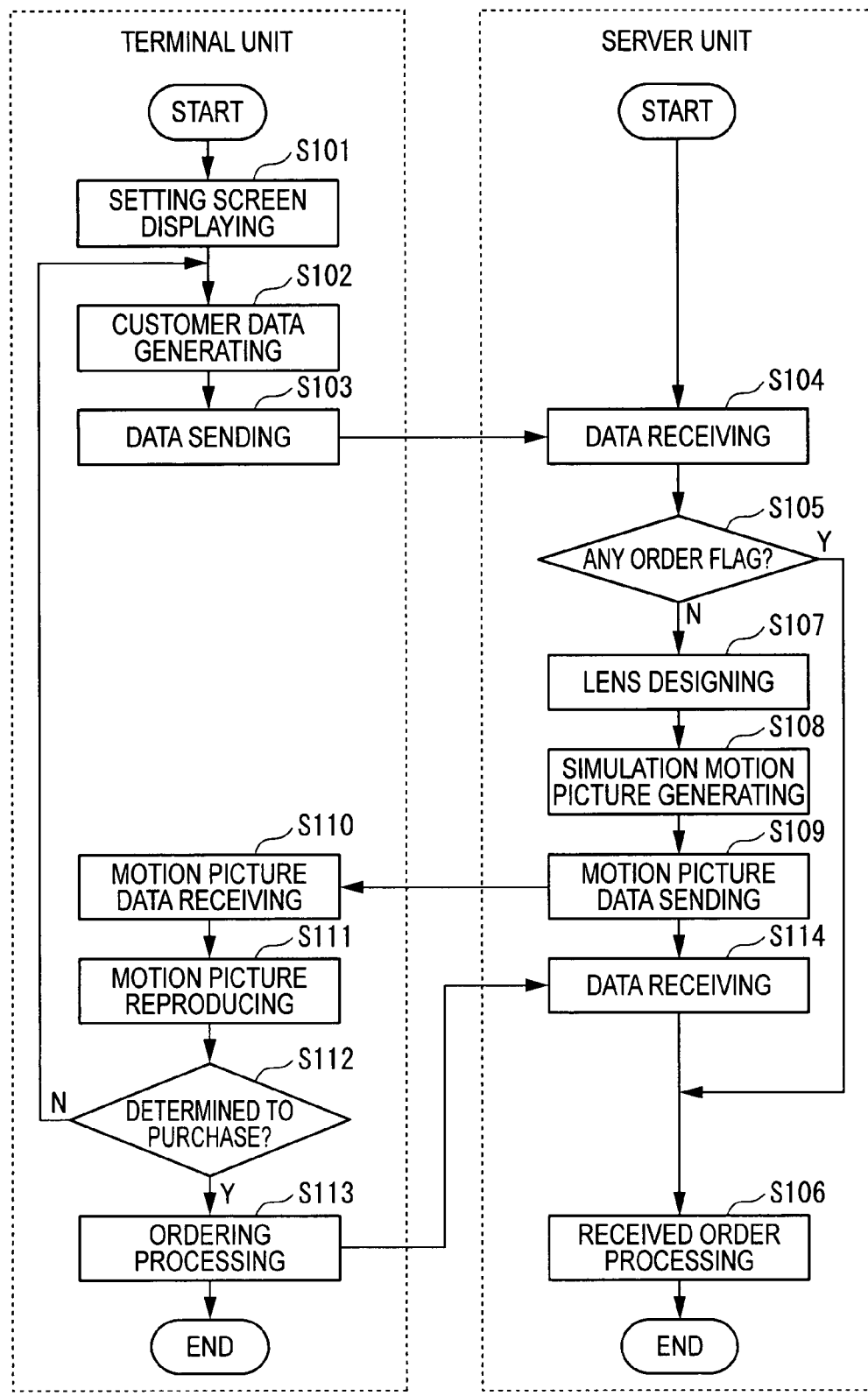
FIG. 15 is a flowchart showing a lens order processing of the lens order system.

A lens order processing in the lens order system 100 will be described with reference to FIG. 15. FIG. 15 is a flowchart showing the lens order processing of the lens order system.

In FIG. 15, when an input signal for staring a processing relating to a lens order is input by an input operation made on the input section 220 by a user, the terminal unit 200 of the lens order system 100 conducts the lens order processing. Specifically, the display controller 264 of the processor 260 of the terminal unit 200 controls the display section 230 to display an input setting screen (Step S101).

When the user such as a lens user and a sales person inputs data in the data display frame displayed on the input setting screen by operating the input section 220, the data recognizer of the processor 260 recognizes the input data. The request data generator 262 of the processor 260 generates the client data 410 based on the recognized data (Step S102). At this time, when an input signal for ordering a lens is input by the input operation made on the input section 220 by the user, the request data generator 262 stores, for example, "1" in the order flag data 417. On the other hand, when an input signal for requesting a generation of a simulation motion picture without ordering a lens is recognized, the request data generator 262 stores, for example, "0" in the order flag data 417.

Subsequently, the data transmitter 263 of the processor 260 controls the communicating section 210 to send the client data 410 generated in Step S102 to a predetermined server unit 300 based on pre-set server destination data (Step S103). At this time, the data transmitter 263 sends the client data 410 and unique data identifying the terminal unit 200 such as the server user data and password data of the server destination data.

On the other hand, when the server unit 300 receives the client data 410 sent from the terminal unit 200 (Step S104), the request data recognizer 361 of the server unit 300 recognizes the client data 410. The request data recognizer 361 judges whether or not an order flag is contained by referring to the order flag data 417 of the client data 410 (Step S105).

In Step S105, when the request data recognizer 361 judges that data indicating that a lens is ordered (e.g. "1") is stored in the order flag data 417, the request data recognizer 361 generates the order reception data 470 based on the client data 410. Specifically, the request data recognizer 361 generates the order reception ID data 471 based on unique data identifying a terminal such as the client ID data 411 and server user data of the client data 410 and recognizes a date when the client data 410 is received to generate the order reception date data 472. In addition, the request data recognizer 361 generates the prescription data 473, the lens design data 474, the usage purpose data 475 and the unique additional data 476 based on the prescription data 412, lens design data 413, usage purpose data 414 and unique additional data 415 of the client data 410. The request data recognizer 361 associates the generated data with each other to generate and readably store the order reception data 470 in the order reception table 460 of the storage 340 (Step S106). When a setting input signal for outputting the order reception data 470 stored in the order reception table 460 is input by an operation on the operation section 320 of the server unit 300, the order reception data output section 364 of the server processor 360 controls the output section 330 to output the order reception data 470. Specifically, the order reception data output section 364 displays the order reception data 470 on the display area of the display and prints the order reception data by a printing machine such as a printer.

On the other hand, in Step S105, when the request data recognizer 361 judges that data indicating that no lens is ordered (e.g. "0") is stored in the order flag data 417, the request data recognizer 361 generates the simulation request data 450 based on the client data 410. Specifically, the request data recognizer 361 generates the request ID data 451 based on unique data such as the client ID data 411 and server user data of the client data 410 for identifying a terminal and recognizes a date when the client data 410 is received to generate the reception date data 452. In addition, the request data recognizer 361 generates the prescription data 453, the lens design data 454, the usage purpose data 455 and the unique additional data 456 based on the prescription data 412, lens design data 413, usage purpose data 414 and unique additional data 415 of the client data 410. The request data recognizer 361 associates the generated data with each other to generate and readably stores the simulation request data 450 in the simulation request table 440 of the storage 340.

Subsequently, the lens design section 362 of the server processor 360 designs a lens based on the simulation request data 450 (Step S107). In other words, the lens design section 362 designs the form of the lens based on the lens design data 454. The lens design section 362 sets a ratio of areas of the lens for seeing a far-distanced, middle-distanced and near-distanced object of the lens based on the usage purpose data 455. Additionally, based on the prescription data 453 and the unique additional data 456, the lens design section 362 sets the thickness and weight of the lens and the curvature of the lens surface for each area for seeing the far, middle and near-distanced object.

The lens design section 362 readably stores the designed ratio of the areas, the thickness and weight of the lens, the curvature of the lens surface, the form of the lens and the like in the memory 350 or the storage 340 as design lens data.

Subsequent to Step S107, the simulation motion picture generator 363 of the server processor 360 generates the simulation motion picture data 430 based on the simulation request data 450 and the design lens data (Step S108).

Specifically, the simulation motion picture generator 363 selects the scene object data 480 that includes the distance data 482 corresponding to the usage purpose of the lens based on the usage purpose data 455, generates a composition image into which these images are combined and image-processes the composition image based on the prescription data 473 and the unique additional data 476 to show the lens user's vision with naked eyes an object of the composition image at a distance of the distance data 482.

The simulation motion picture generator 363 selects the lens object data 490 corresponding to the lens design data 454 and superposes the lens image data 493 of this lens object data 490 on the above-created composition image.

Based on the design lens data, the simulation motion picture generator 363 image-processes the superposing portion 510 of the lens image data 493 and the image data 520, 530, 540 based on the scene object data 480 of the composition image to show the lens user's vision an object at the distance of the distance data 482 through the lens.

The simulation motion picture generator 363 moves the lens image data 493 on the composition image and sequentially image-processes the superposing portion 510 in accordance with the movement of the lens image data 493 to generate a composition motion picture in which the image data 520, 530, 540 out of the superposing portion 510 is restored to show the lens user's vision with naked eyes an object located at a position apart by a distance of the distance data 482. At this time, the simulation motion picture generator 363 computes distortion of the image data caused by the movement of the lens image data 493 based on the design lens data, the prescription data 453 and the unique additional data 456 to reflect the distortion on the superposing portion 510.

The simulation motion picture generator 363 generates the simulation motion picture data 430 that includes the above-generated composition motion picture as the motion picture data 432. Subsequently, based on the unique data identifying the terminal unit 200 such as the server user data sent with the client data 410 in Step S104, a processing is conducted for sending the generated simulation motion picture data 430 to the predetermined terminal unit 200 (Step S109).

In the terminal unit 200, when the simulation motion picture data 430 sent from the server unit 300 is received (Step S110), the data acquiring section 261 recognizes the simulation motion picture data 430 and a processing is conducted for readably storing the simulation motion picture data 430 in the simulation motion picture table 420.

When a reproduction button for reproducing a motion picture of the input setting screen displayed in Step S202 is selected and a request signal for requesting a reproduction of the simulation motion picture data 430 is accordingly input, the display controller 264 of the processor 260 controls the display section 230 to display the motion picture data 432

(FIGS. 6 to 8) on the display area (Step S111). At this time, the display controller 264 recognizes the client ID data 411 input by the input setting screen and the simulation motion picture data 430 including the motion picture ID data 431 associated with the client ID data 411 to reproduce the motion picture data 432 of the simulation motion picture data 430.

As described above, the motion picture data 432 shows the lens user's vision of an object with naked eyes and with the ordered lens based on the vision data of the lens user, the lens user can judge whether or not the ordered lens meets his demands by checking the motion picture data 432.

Subsequent to the check on the motion picture data 432, the data acquiring section 261 of the processor 260 judges whether or not the order flag data 417 is input by an input operation made on the input section 220 by the user (Step S112).

In Step S112, when the order button relating to an lens order on the input setting screen is not selected by an input operation made on the input section 220 by the user but an operation for editing the data in the data display frame is conducted, the processing returns to Step S102 where the request data generator 262 of the processor 260 modifies the client data 410.

On the other hand, in Step S112, when the order button relating to an lens order on the input setting screen is selected by an input operation made on the input section 220 by the user to input a setting for ordering a lens, the request data generator 262 generates the client data 410 in which data indicating that a lens is ordered (e.g. "1") is stored in the order flag data (Step S113). The generated client data 410 is sent to the server unit 300 together with the unique data such as the server user data for identifying the terminal unit 200.

When receiving the client data 410 generated in Step S113 (Step S114), the server unit 300 conducts the processing in Step S106. Specifically, the request data recognizer 361 of the server processor 360 generates the order reception data 470 based on the client data 410 and readably stores the order reception data 470 in the order reception table 460. When the input signal for outputting the order reception data 470 is input, the output section 330 is controlled to output the order reception data 470.

Subsequent to Step S106, the server unit 300 ends the lens order processing. Alternatively, the server unit 300 is set on standby, where the server unit 300 waits for receiving the client data 410 from the terminal unit 200.

On the other hand, the terminal unit 200 ends the lens order processing subsequent to Step S113.

Effects and Advantages of Lens Order System

As described above, the data acquiring section 261 in the lens order system 100 according to the above-described exemplary embodiment of the terminal unit 200 connected via the network 110 with the server unit 300 recognizes data input from the input section 220; the request data generator 262 generates the client data 410; and the generated client data 410 is sent to the server unit 300.

The server unit 300 recognizes the received client data 410; and when data indicating that no lens is ordered is stored in the order flag data 417 of the client data 410, the server unit 300 generates the simulation request data 450 based on the client data 410. Based on the simulation request data 450, the lens design section 362 of the server unit 300 designs the lens and generates the design lens data. Based on the simulation request data 450, the simulation motion picture generator 363 of the server unit 300 recognizes the scene object data 480 and the lens object data 490. Based on the scene object data 480 and the lens object data, the lens image data 493 is superposed and moved on a predetermined composition image. And the simulation motion picture data 430 having the motion picture data 432, in which the superposing portion 510 of the lens image data 493 and the composition image data is image-processed based on the design lens data to show the lens user's vision of the composition image data, is generated to be sent to the terminal unit 200.

The terminal unit 200 controls the display section 230 by the display controller 264 and conducts a processing for reproducing the motion picture data 432 of the simulation motion picture data 430.

Further, when the request data generator 262 of the terminal unit 200 recognizes an input signal for ordering a lens, the request data generator 262 generates the client data 410 in which information for ordering a lens is stored in the order flag data 417 and sends the generated client to the server unit 300. In the server unit 300, when the request data recognizer 361 recognizes that information for ordering a lens is stored in the order flag data 417 of the client data 410, the request data recognizer 361 generates the order reception data 470 based on the client data 410.

Accordingly, with the simulation motion picture data 430, the lens user can check the vision through the lens that he is going to order before ordering. Hence, inconvenience such as a mismatch between the lens desired by the lens user and the actually manufactured lens can be avoided, so that the lens that the lens user truly desires can be securely ordered.

Since the server unit 300 is adapted to generate the motion picture data 432 of the simulation motion picture data 430 so that the terminal unit 200 is only required to reproduce the generated simulation motion picture data 430, the processing load placed on the terminal unit 200 can be reduced. Hence, regardless of the processing capability of the terminal unit 200, the simulation motion picture data 430 can be reproduced, thereby appropriately assisting lens-selection of the lens user.

The data sent from the terminal unit 200 via the network 110 to the server unit 300 is data of small size such as the client data 410 and only the simulation motion picture data 430 is sent from the server unit 3 to the terminal unit 200, communication load in data transmission can be reduced, thereby speeding up the processing. Accordingly, it is possible to appropriately assist the lens user to select a lens, thereby speeding up the ordering processing of the lens.

The lens design section 362 of the server processor 360 designs the lens based on the lens prescription data stored in the prescription data 412 of the client data 410. Hence, the lens design section 362 can design a lens that matches the lens prescription desired by the lens user. Accordingly, the lens can be set exactly how the lens user desires.

The simulation motion picture generator 363 image-processes the superposing portion 510 based on the design lens data. Accordingly, owing to the simulation motion picture data 430 reproduced on the terminal unit 200, the lens user can easily check the vision through the lens of his lens prescription data. Hence, since the lens user can easily check the desired lens before manufacturing the lens, it is possible to manufacture the lens desired by the lens user.

Based on the vision data of the prescription data 453 of the simulation request data 450, the simulation motion picture generator 363 creates the motion picture data 432 in which the lens image data 493 is superposed on the composition image corresponding to the vision of the lens user with naked eyes.

Accordingly, by reproducing the motion picture data 432 on the terminal unit 200, the lens user can check and compare the vision of the to-be-seen object with naked eyes and the vision with the lens. Hence, it is possible to easily check the performance of the lens or whether or not the lens matches with his preference based on the motion picture data 432, so that the lens truly desired by the lens user can be appropriately ordered.

The simulation motion picture generator 363 image-processes the scene object image data 483 of the scene object data 480 based on the vision data of the prescription data 453 to show the lens user's vision of the object with naked eyes.

Since the simulation motion picture generator image-processes the scene object image data 483, a plurality of pieces of scene object image data 483 corresponding to the vision data can be generated, thereby reducing the volume of the scene object data 480 stored in the scene object table 480A and promoting more efficient use of the storage area of the storage 340.

Herein, based on the distance data 482 of the scene object data 480, the simulation motion picture generator 363 image-processes the scene object image data 483 based on the vision data to show the lens user's vision of the object of the scene object image data 483 disposed at a distance of the distance data 482.

Hence, it is possible to show a difference depending on the distance of the object on the composition image, so that the motion picture data 432 that is closer to the actual vision can be created. By seeing such motion picture data 432, the lens user can easily check the characteristics of the lens, thereby providing appropriate assistance for selecting a lens.

Based on the lens design data 454, the lens design section 362 of the server processor 360 designs the lens and generates the design lens data.

Accordingly, the lens can be designed into a form that the lens user desires. Since the simulation motion picture generator 363 recognizes the lens object data 490 corresponding to the lens design data and generates the motion picture data 432 in which the lens image data 493 is superposed on the composition image, the lens user can see the motion picture data 432 and judge whether or not the lens form is appropriate before producing the lens. Accordingly, the lens having an appropriate form that fits the lens user can be ordered.

The lens design section 362 designs the lens so as to correspond to the usage purpose data 455 and generates the design lens data and the simulation motion picture generator 363 selects the scene object data 480 having the distance data 482 corresponding to the usage purpose data 455.

Hence, the lens design section 362 can design the lens so as to have the distance characteristics corresponding to the usage purpose of the lens of the lens user. The simulation motion picture generator 363 generates the composition image with which the scene object image data 483 corresponding to the usage purpose of the lens by the lens user is combined, and the simulation motion picture generator 363 image-processes the superposing portion 510 of the lens image data 493 based on the design lens data set by the lens design section 362. Hence, it is possible to generate the motion picture data 432 corresponding to the lens usage purpose of the lens user in a manner closer to the actual vision, thereby more appropriately assisting lens-selection of the lens user.

The usage purpose data 455 includes the usage distance data on a distance from the lens to the to-be-seen object. Hence, the distance from the lens to the object can be more clearly recognized, so that the lens design section 362 can design the lens that appropriately matches with the lens usage purpose of the lens user. Since the simulation motion picture generator 363 generates the motion picture data 432 in which the image data 520, 530, 540 corresponding to the lens usage purpose is image-processed, the lens user can check the lens condition corresponding to the lens usage purpose by checking the motion picture data 432, thereby enabling a more appropriate selection of a lens.

Further, the simulation motion picture generator 363 generates the motion picture data 432 in which the lens image data 493 is moved on a composition image.

Hence, it is possible to simulate distortion and the like generated by a movement of the lens while the lens user sees the composition image with the lens corresponding to the design lens data. Accordingly, by checking the motion picture data 432, it is possible to more appropriately simulate the usage of the lens, thereby more appropriately assisting the lens user to select and order a lens appropriate for the lens user.

Modifications of Exemplary Embodiment

An aspect of the invention is not limited to the exemplary embodiment, but the invention also includes below-described modifications and the like as long as an object of the invention can be achieved.

In the above exemplary embodiment, the simulation motion picture generator 363 image-processes the scene object image data 483 of the scene object data 480 based on the vision data, but the architecture is not limited thereto. For example, the scene object table 480A may be adapted to store more specifically classified scene object data 480 based not only on the distance data 482 but also on the vision data such as the visual power and the astigmatic power and the simulation motion picture generator 363 may be adapted to select the scene object data 480 in correspondence with the vision data. In such an architecture, it is not necessary to image-process the scene object image data 483 based on the vision data, so that the processing load placed on the server processor 360 of the server unit 300 can be reduced. Accordingly, the time required for generating the simulation motion picture data 430 can be reduced, thereby realizing a faster lens order processing.

As another exemplary modification, the whole scene object data 480 may not be image-processed by the vision data, but a simulation of the vision through the lens may be provided by image-processing only a portion superposed with the lens image data 493 based on the vision data and the design lens data. With the displayed motion picture data generated by the above-described image processing, the lens user can check the vision with the lens as compared with an ideal vision (the vision of an emmetrope) of the image data 520, 530, 540.

It is effective to check the actual vision of the lens relative to the ideal vision for evaluating of the lens design. This is particularly effective for a patient with progressed ametropy (progressed myopia, progressed hyperopia and progressed astigmatism). In a case of progressed ametropy, when the image data 520, 530, 540 is image-processed by the vision data, the original image data 520, 530, 540 is extremely blurred or distorted, thereby making it difficult to recognize the image data 520, 530, 540.

Further, in the above-described exemplary embodiment, the client data 410 includes the order data 416; information indicating that the lens is ordered is stored in the order flag data 417 of the order data 416; and the client data 410 is sent to the server unit 300 to order the lens. However, the architecture is not limited thereto. For example, the order data 416 may be generated independently of the client data 410.

In this case, by adding the design lens data to the order data 416 to be sent to the server unit 300, it is possible to omit procedure for re-designing the lens when manufacturing by the manufacturer, thereby realizing a faster manufacturing of the lens.

As described above, the order reception data output section 364 of the server unit 300 may control the output section 330 to display the order reception data 470 on the display, may print out the order reception data 470 by a printing machine such as a printer or may conduct another output control. The order reception data output section 364 may output the order reception data 470 directly to a lens manufacturing line of the manufacturer such that the lens can be automatically manufactured based on the order reception data 470 by the lens manufacturing line.

Although the terminal unit 200 is a personal computer set at a shop such as a lens shop in the above exemplary embodiment, the terminal unit 200 may be a personal computer of home use or an electronic device such as a portable phone which can communicate via the network 110 with the server unit 300.

In the exemplary embodiment, the server unit 300 is provided on the manufacturer facility, but, for example, a large server unit may be provided at a head shop of a selling shop i.e. at a relaying position between the shop and the manufacturer.

The simulation motion picture generator 363 is adapted to generate the motion picture data 432 in the exemplary embodiment, but composition image data may be created in which the lens image data 493 is superposed on a composition image. In this architecture, the data size sent from the server unit 300 to the terminal unit 200 can be made smaller, so that communication load can be further reduced.

In the above exemplary embodiment, the terminal unit 200 sends the client data 410 that includes the prescription data 412 having the vision data and the lens prescription data. However, only the vision data may be sent to the server unit 300 and the lens may be designed in the server unit 300 in accordance with the vision data. In this architecture, by checking the motion picture data 432 of the simulation motion picture data 430 sent from the server unit 300, it is possible to judge whether or not the designed lens is suitable for the lens user.

The lens design data 413 may be set by selecting from plural types of frame image, or the lens image stored in advance in the storage 240 of the terminal unit 200 in accordance with the input setting by the user or may be set by selecting from plural types of frame image or the lens image sent from the server unit 300.

Although the server unit 300 conducts both of generation processing of the simulation motion picture data 430 and an order processing, a plurality of server units may share these processing. In short, when judging that no order data 416 is input, the terminal unit 200 sends the client data to one of the server units, which generates the simulation motion picture data 430 based on the client data 410 and sends the generated simulation motion picture data 430 to the terminal unit 200. On the other hand, when judging that the order data 416 is input, the terminal unit 200 sends the client data to the other server unit which conducts an order processing based on the sent client data 410. Similarly to the above-described exemplary embodiment, this architecture can appropriately assist the lens order processing of the lens user while reducing the processing load on the terminal unit 200 and communication load. The two server units shares the simulation motion picture generating processing and the order processing, processing load placed on each server unit can be reduced.

Although the display controller 264 of the terminal unit 200 is adapted to display the input setting screen on the display area of the display section 230 to prompt a data input in the exemplary embodiment, the input setting screen may be a web browser. In this case, an input setting file for acquiring data which forms the input setting screen and is created by, for example, CGI (Common Gateway Interface) may be stored in the server unit in an accessible manner via a network such that the data can be input by accessing the input setting file provided to the terminal unit 200, thereby sending the client data 410 to the server unit 300.

The above functions are structured as a program in the exemplary embodiment but may be provided as hardware such as a circuit board or an IC (Integrated Circuit) or as another form. In the architecture in which the functions are read from a program or a recording medium, the handling can be made easy, thereby easily expanding the usage.

In addition, a specific structure and procedure when implementing an aspect of the invention can be changed to another structure and the like without departing from the range of an object of the invention.

A lens order system according to the invention is applicable to a lens order system, a lens order method, a lens order program and a recording medium storing the lens order program by which a lens such as a spectacles lens is ordered.

What is claimed is:

1. A lens order system, comprising:
a server unit including:
   a data recognizer that recognizes lens design detail data on setting details of a lens;
   an image data recognizer that recognizes image data on an image;
   a lens design section that designs the lens based on the lens design detail data;
   an image processor that creates processed image data in which lens image data on an image of the designed lens is superposed on the image data and a superposing portion of the image data and the lens image data is image-processed to show a vision of the image data through the designed lens; and
   an order reception section that recognizes order data on an order of the designed lens and generates order reception data; and
a terminal unit connected with the server unit in a data transmittable manner, the terminal unit including:
   a data acquiring section that acquires the lens design detail data;
   a display controller that recognizes and displays on a display the processed image data sent from the server unit; and
   an order section that generates the order data,
wherein the lens design detail data includes vision data on a vision of a lens user, and
based on the vision data, the image processor generates processed image data in which the image data is image-processed to show the vision of the lens user with naked eyes, superposes the lens image data on the generated processed image data and image-processes a superposing portion of the processed image data and the lens image data to show the vision of the image data of the lens user through the designed lens.

2. The lens order system according to claim 1, wherein
the lens design detail data includes lens prescription data on a prescription for a lens of the lens user, and
the lens design section designs the lens based on the lens prescription data.

3. The lens order system according to claim 1, wherein
the lens design detail data includes lens form design data on a design of a lens form, and
the lens design section designs the lens into a form based on the lens form design data.

4. The lens order system according to claim 1, wherein
the lens design detail data includes lens usage purpose data on a usage purpose of the lens of the lens user,
the lens design section designs the lens corresponding to the usage purpose of the lens based on the lens usage purpose data, and
the image data recognizer recognizes the image data corresponding to the usage purpose of the lens based on the lens usage purpose data.

5. The lens order system according to claim 4, wherein
the lens usage purpose data is usage distance data on a distance from a to-be-seen object to the lens user wearing the lens.

6. The lens order system according to claim 1, wherein
the image processor superposes the lens image data on the image data and generates motion picture data moved on the image data.

7. A lens order method, comprising:
in a terminal unit, which comprises a computer executing operations of the terminal unit, and is connected with a server unit in a data transmittable manner:
acquiring lens design detail data and sending the acquired lens design detail data to the server unit,
in the server unit which comprises a server processor which executes operations of the server unit:
recognizing lens design detail data on setting details of a lens sent from the terminal unit, recognizing image data on an image;
designing the lens based on the lens design detail data, superposing lens image data on an image of the designed lens on the image data;
image-processing a superposing portion of the image data and the lens image data to show a vision of the image data through the designed lens; and
sending the processed image data to the terminal unit, in the terminal unit:
recognizing the processed image data sent from the server unit to be displayed by a display;
generating order data on an order of the designed lens; and
sending the generated order data to the server unit, and in the server unit:
receiving the order data and generating received data,
wherein the lens design detail data includes vision data on a vision of a lens user, and
the image-processing comprises, based on the vision data, generating processed image data in which the image data is image-processed to show the vision of the lens user with naked eyes, superposing the lens image data on the generated processed image data and image-processing a superposing portion of the processed image data and the lens image data to show the vision of the image data of the lens user through the designed lens.

* * * * *